United States Patent [19]

Gandolfi et al.

[11] Patent Number: 5,021,436
[45] Date of Patent: Jun. 4, 1991

[54] 2-THIOMETHYL-SUBSTITUTED-1,4-DIHYDROPYRIDINES, AND PHARMACEUTICAL COMPOSITIONS CONTAINING SAME AND ANTIHYPERTENSIVE PROPERTIES

[75] Inventors: Carmelo A. Gandolfi; Marco Frigerio; Silvano Spinelli; Odoardo Tofanetti; Sengio Tognella, all of Milan, Italy

[73] Assignee: Boehringer Mannheim Italia, S.p.A., Milan, Italy

[21] Appl. No.: 413,896

[22] Filed: Sep. 28, 1989

Related U.S. Application Data

[62] Division of Ser. No. 889,379, Jul. 25, 1986.

[30] Foreign Application Priority Data

Aug. 6, 1985 [IT] Italy ............... 21876 A/85
Jun. 27, 1986 [IT] Italy ............... 20965 A/86
Jun. 27, 1986 [IT] Italy ............... 20966 A/86

[51] Int. Cl.⁵ ............... A61K 31/455; C07D 211/86
[52] U.S. Cl. ............... 514/356; 544/360; 546/263; 546/268; 546/276; 546/277; 546/278; 546/321
[58] Field of Search ............... 546/321, 322; 514/356

[56] References Cited

U.S. PATENT DOCUMENTS 4,892,881  1/1990  Alker et al. ............... 514/356
4,971,984 11/1990  Frigerio et al. ............... 514/356

Primary Examiner—Alan L. Rotman
Attorney, Agent, or Firm—Armstrong, Nikaido, Marmelstein, Kubovcik & Murray

[57] ABSTRACT

Compounds of formula I

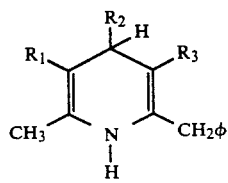

wherein
$R_1$ is an alkoxycarbonyl group, acetyl, benzoyl, cyano, nitro or aminocarbonyl;
$R_2$ is an optionally substituted aryl or hetaryl group;
$R_3$ is an alkoxycarbonyl group;
$\phi$ is a thio residue such as alkylthio, cycloalkylthio, arylthio, heteroarylthio, aminoalkylthio,
are described.

Compounds I are useful in human therapy as antihypertensive, antiulcer, antithrombotic, antiischaemic agents.

8 Claims, No Drawings

2-THIOMETHYL-SUBSTITUTED-1,4-DIHYDROPYRIDINES, AND PHARMACEUTICAL COMPOSITIONS CONTAINING SAME AND ANTIHYPERTENSIVE PROPERTIES

This is a division of application Ser. No. 889,379, filed July 25, 1986.

The present invention relates to 2-thiomethyl-substituted-1,4-dihydropyridines, to a method for their preparation and to pharmaceutical composition containing them.

The compounds of the invention have the following formula I

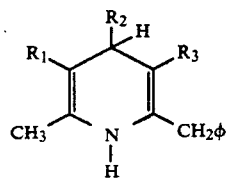

(I)

wherein:

$R_1$ represents acetyl, benzoyl, cyano, nitro groups, or groups of formula $CO_2R_5$ or $CONR_6R_7$;

$R_2$ is a phenyl ring unsubstituted or substituted with one or more $C_1$–$C_6$ alkyl, $C_1$–$C_6$ alkoxy, halo-$C_1$–$C_4$ alkoxy, halo-$C_1$–$C_6$ alkyl, halogen, nitro, cyano, $C_1$–$C_6$ alkoxycarbonyl, $C_1$–$C_6$ alkylthio, $C_1$–$C_6$ alkylsulphyl; pentafluorophenyl; α- or, β-naphtyl; a five- or six-membered he-terocyclic ring; α-benzo[2,3-b]-1,4-dioxan-α-yl; α-benzofuroxanyl;

$R_3$ is a group of formula $CO_2R_5$;

φ is selected in the group consisting of:

a) a thiol group free or esterified with a $C_2$–$C_{12}$ fatty acid;

b) a thiouronium salt of formula $-S-C(=NR_8)NR_9R_{10}^{(+)}Y^{(-)}$ wherein $Y^{(-)}$ is a pharmaceutically acceptable anion and $R_8$, $R_9$, $R_{10}$, which are the same or different, are hydrogen or $C_1$–$C_4$ alkyl group;

c) a thioether residue $-S(O)_n-R_4$ wherein n is zero, 1 or 2 and $R_4$ is selected from the group consisting of:

a') a $C_1$–$C_5$ alkyl, a $C_3$–$C_5$ alkenyl or a $C_3$–$C_5$ alkynyl unsubstituted groups;

b') a $C_3$–$C_7$ cycloaliphatic residue;

c') aryl group, optionally substituted by one or more substituents selected from the group consisting of halogen, hydroxy, nitro, cyano, acetyl, $C_1$–$C_6$ alkyl, halo-$C_1$–$C_6$ alkyl, amino, monoalkylamino, dialkylamino, carboxy, $C_1$–$C_4$-alkoxycarbonyl, p-(imidazol-1-yl), $C_1$–$C_3$-alkoxy, $C_1$–$C_3$-alkylthio, and $C_1$–$C_{12}$ acylamino groups;

d') a saturated or unsaturated heterocyclic ring, unsubstituted or substituted by one or more substituents selected from the group consisting of halogen, $C_1$–$C_6$ alkyl, $C_1$–$C_6$ alkoxy, halo-$C_1$–$C_6$ alkyl, alkyl, monoalkylamino, dialkylamino, cyano, carboxy, $C_1$–$C_4$ alkoxycarbonyl, $-CONR_6R_7$, aryloxyalkyl and aryl groups;

e') a mono- or a poly-substituted $C_2$–$C_{12}$ alkyl chain, optionally interrupted by one or more oxygen or sulphur atoms wherein the substituents are selected from the group consisting of hydroxy, thio, cyano, halogen, amino, monoalkylamino, dialkylamino, $C_1$–$C_4$ alkoxy, $C_1$–$C_4$ alkylthio, $C_1$–$C_4$ acyloxy, $C_1$–$C_4$ acylthio, $CO_2H$, $C_1$–$C_4$ alkoxycarbonyl, $CONR_6R_7$, a $C_3$–$C_7$ cycloaliphatic residue, arylresidue or a saturated or unsaturated heterocyclic residue said residues having the above defined meanings;

f') a $C_2$–$C_{12}$ oxygenated alkyl chain of formula $-(CH_2)_n-A-(CH_2)_p-B$ wherein A may be a cis- or trans-oxirane ring and a masked or unmasked carbonyl moiety and B is hydrogen, $C_1$–$C_4$ alkyl, cyano, carboxy, $C_1$–$C_4$ alkoxycarbonyl, $CONR_6R_7$ groups, amino, monoalkylamino, a $C_3$–$C_7$ cycloaliphatic residue, an aryl or a saturated or unsaturated heterocyclic residues, said residues having the above defined meanings;

g') a group of formula:

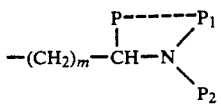

wherein P may be hydrogen, $C_1$–$C_8$ alkyl and a group of formula $-(CH_2)_{p1}-W$; $NP_1P_2$ is a primary, secondary or tertiary amino group, an amidic or imidic residue wherein $P_1$ and $P_2$, which are the same or different, may be hydrogen, $C_1$–$C_6$ alkyl, $-(CH_2)_{p1}-W$ or $C_1$–$C_6$ acyl group; $P_1$ and $P_2$, taken together with the nitrogen atom to which they are linked, may form a cyclic amide or the

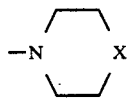

residue; P, taken together with $P_2$ and the nitrogen atom to which $P_1$ is linked, may form a pyrrolidine or a piperidine ring;

W is selected from the group consisting of hydrogen, methyl, saturated or unsaturated heterocyclic ring, a $C_3$–$C_7$ cycloalkyl ring, a phenyl ring unsubstituted or substituted by one or more substituents selected from the group of halogen, nitro, p-imidazol-1-yl, hydroxy, $C_1$–$C_3$ alkoxy and $CH_2-NP_4P_5$; X may be $(CH_2)_{p1}$, $O,N-P_3$; $P_3$ is hydrogen, methyl, $C_1$–$C_3$ acyl, diphenylmethane or bis-(4-fluorophenyl)methane; $P_4$ and $P_5$, which are the same or different, may be hydrogen, $C_1$–$C_4$ alkyl or taken together with the nitrogen atom to which they are linked, $P_4$ and $P_5$ form the radical

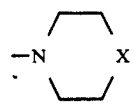

wherein X is as above defined;

$R_5$ is hydrogen, a cation of ammonium or of an alkaline metal, a $C_1$–$C_6$ alkyl chain unsubstituted or substituted by hydroxy, amino, monoalkylamino, dialkylamino, or $C_1$–$C_6$ alkoxy groups; $C_3$–$C_6$ alkenyl; an optionally substituted aryl or $C_1$–$C_4$ aralkyl group;

each of $R_6$ and $R_7$, which are the same or different, may be hydrogen, $C_1$–$C_6$ alkyl, benzyl or aryl;

$n_1$ is an integer from 1 to 6; m is an integer from 1 to 3;

p is zero or an integer from 1 to 6 and $p_1$ is zero or an integer from 1 to 3;

with the proviso that when $\phi$ is a thioether substituent of formula $-S(O)_n-R_4$ and $R_4$ is a $C_1-C_5$ alkyl group, n is different from zero.

Also the pharmaceutically acceptable salts as well as the optical antipodes, i.e. the enantiomers, the possible geometric isomers, diastereoisomers and mixtures thereof are included in the scope of the present invention.

The alkyl, alkenyl, alkoxy and alkanoyloxy groups are branched or straight chain groups.

A halo-$C_1-C_6$ alkyl group is preferably trihalo-$C_1-C_6$ alkyl, in particular trifluoromethyl.

A halo-$C_1-C_4$ alkoxy group is preferably $-OCHF_2$.

A $C_1-C_6$ alkyl group is preferably methyl, ethyl, isopropyl or t-butyl.

A $C_2-C_{12}$ alkanoyl group is preferably acetyl, propionyl, hexanoyl or heptanoyl.

An aryl group is preferably phenyl.

A $C_3-C_5$ alkenyl group is preferably allyl.

A $C_3-C_5$ alkynyl group is preferably propargyl.

A $C_3-C_7$ cycloaliphatic radical is preferably cyclopentyl, cyclohexyl and cycloheptyl.

A monoalkyl amino group is preferably a methyl-, ethyl-, isopropyl- or benzyl-amino group.

A dialkylamino group is preferably a linear group such as dimethyl-, diethyl-, benzyl-, methyl-amino group; or a cyclic group such as pyrrolidine-1-yl;piperidine-1-yl, morpholin-1-yl, 4-methyl-piperazine-1-yl, 4-phenyl-pi-perazine-1-yl-4-diphenylmethane-piperazine-1-yl, 4-bis(p-fluorophenyl)methane-piperazine-1-yl, 4-ethyl-piperazine-1-yl, 4-(2'-hydroxyethyl)piperazine-1-yl.

A $C_1-C_4$ alkoxycarbonyl is preferably methoxy-, ethoxy- and ter-butoxy-carbonyl group.

A $C_1-C_3$ alkoxy is preferably methoxy and isopropoxy.

A $C_1-C_3$ alkylthio is preferably methylthio and isopropylthio.

A masked carbonyl function is preferably an acetal of formula $>C(O-C_{1-3}alkyl)$ and more preferably a 1,3-dioxolane or 1,3-dioxane ring wherein one or both the oxygen atoms may be optionally substituted by sulphur atoms.

When $R_2$ is a five- or six- membered heterocyclic ring, it is preferably pyridyl, furanyl or thienyl; when $R_4$ is an heterocyclic ring, it may be either a heteromonocyclic ring or a heterobicyclic ring containing at least one heteroatom selected from the group consisting of N, S, and O.

Examples of preferred heteromonocyclic residues are α, β, and γ-pyridyl; tetrahydrofuryl; thienyl; α-pyridyl-N-oxide; 3-hydroxy-α-pyridyl; 2 and 4-pyrimidinyl; 1H-1,2,4-triazol-3-yl; 1H-1,2,4-triazol-4-yl; 2-thiazolyl; 1-methyl-tetrazol-5-yl; 2-methyl-1,3,4-thiadiazol-5-yl; 5-amino-1,3,4-thiadiazol-2-yl; 2-amino-1,2,4-triazol-5-yl; 2-hydantoinyl; 2-imidazolinyl; 4-methyl-5-trifluoromethyl-4H-1,2,4-triazolin-3-yl; 1-methyl-imidazol-2-yl; 1-phenyl-1H-tetrazol-5-yl; 4,5-diphenyl-4-oxazolyn-2-yl; 5,5-disubstituted-hydantoin-2-yl; 4-phenoxymethyl-5-carboxy-imidazol-2-yl and esters thereof with $C_1-C_4$ lower alcohols; 1,4,5,6-tetrahydro-pyrimidin-2-yl;4-substituted-imidazol-2-yl; 5-carboxy-4-substituted-imidazol-2-yl; pyrimidin-2-yl and derivatives thereof with methyl, amino, oxo and/or carboxy groups in 4 and 6 positions of the pyrimidine ring; pyrimidin-4-yl; pyrimidin-6-yl; 2,6-diamino-pyrimidin-4-yl; tetrahydropyran-2-yl; (3,4,5-triacetoxy-6-acetoxymethyl)tetrahydropyran-2-yl; 5-carboethoxy-4-oxo-pyrimidine-2-yl; 6-propyl-4-hydroxy-pyrimidin-2-yl and 6-propyl-4-amino-pyrimidin-2-yl.

Examples of preferred heterobicyclic residues are: 4-(3H)-quinazolin-4-one-2-yl; quinazolinyl-2; 4-aminopyrazol [3,4-d] pyrimidin-2-yl; 6-purinyl; 6,8-dihydroxy-2-purinyl; benzothiazol-2-yl; benzoxazol-2-yl; benzimidazol-2-yl and derivatives thereof substituted in the benzene ring with alkoxy and halo substituents; quinolin-2-yl; 7-trifluoromethyl-quinolin-4-yl.

The aryl and the heterocyclic radical of $R_4$ may be linked to the sulfur atom by means of an alkyl chain, this alkyl chain being preferably a $C_1-C_4$ alkyl chain.

When $R_4$ is a mono-or a poly- substituted $C_2-C_{12}$ alkyl chain, optionally interrupted by one or more oxygen or sulphur atoms, this chain is preferably the residue of $C_2-C_{12}$ alkyl thiols such as: 3-phenyl-propane-1-thiol, 3-cyclohexyl-propane-1-thiol, 3-cyclopentyl-propane-1-thiol, 2-propene-1-thiol, 2-propyn-1-thiol, 2-mercapto-1-ethanol, and ether or thioethers thereof such as 2-methoxy-ethane-1-thiol, 2-ethoxy-ethane-1-thiol, 2-propoxyethane-1-thiol, 2-isopropoxy-ethane-1-thiol, 2-pentoxyethane-1-thiol, 2-phenoxyethane-1-thiol, 3-phenoxy-propane-1-thiol, 2-methylthio-ethane-1-thiol, 2-ethylthio-ethane-1-thiol, etc.; 3-mercapto-1,2-propanediol and 1,2-acetals thereof; 2-furyl-methane-thiol, 2-(2-furyl)ethane-1-thiol, 2-(2-thienyl)ethane-thiol, 2-(3-thienyl)ethane-1thiol, 2-(4-methyl-5-thiazol)ethane-1-thiol, 2-(imidazol-1-yl)ethane-1-thiol, 2-(β-pyridyl)ethane-1-thiol, 3-(imidazol-1-yl)propane-1-thiol, 2-(γ-pyridyl)ethane-1-thiol, 2-(pyrrol-1-yl)ethane-1-thiol, 2-(2,5-dimethyl-pyrrol-1-yl)ethane-1-thiol, 3-(2,5-dimethyl-pyrrol-1-yl)propane-1-thiol; alkylamino-alkylthiols such as 2-dimethylaminoethane-1-thiol, 2-diethylamino-ethane-1-thiol, 2-butylamino-ethane-1-thiol, 2-(N-morpholine)ethane-1-thiol, 2-(N-pyrrolidinyl)ethane-1-thiol, 2-(N-piperidinyl)ethane-1-thiol, 2-(4'-N-substituted-piperazin-1-yl)ethane-1-thiol; aminoalkylthiols such as cysteamine, homocysteamine, 4-aminobutane-1-thiol and derivatives thereof wherein the aminogroup is protected as BOC, acylamide or cyclic imide; 3-amino-, 3-monoalkylamino and 3-dialkylaminopropane-1-thiols; mercaptoacids i.e. thioglycolic, thiolactic and thiomalic acid and derivatives thereof such as esters, amides and nitriles; α-amino acids containing thiol groups such as cystein, homocystein and polypeptides obtained starting from these aminoacids as well as glutathion; $R_5$ is preferably methyl, ethyl or isopropyl; $R_6$, $R_7$, $R_8$, $R_9$ and $R_{10}$ are preferably hydrogen.

When one of $P_1$ and $P_2$ is an acyl group, it is preferably a $C_1-C_4$ acyl, chloroacetyl, trichloroacetyl, trifluoroacetyl, tert-butoxycarbonyl (BOC), optionally substituted benzoyl with nitro or methoxy groups.

When $NP_1P_2$ is a cyclic imide, it is preferably a cyclic imide obtained starting from succinic, glutaric, maleic, 2,3-diphenylmaleic, phtalic, hexahydro or tetrahydrophtalic acids.

When A is a masked carbonyl function it is preferably 1,3-dioxolane and a dimethoxy or diethoxyacetal.

The non toxic salts that are pharmaceutically acceptable include the hydrochlorides, hydrobromides, hydroiodides, (lower)alkylsulfates, (lower)alkyl and aryl sulfonates, phosphates, sulfates, maleates, fumarates, succinates, tartrates, citrates, and others commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent of the character of the acid used in the preparation of the salt.

Specific examples of preferred compounds of the invention are 6-methyl-3,5-dicarboethoxy-4-(m-nitrophenyl)-2-methylsulphinylmethyl-1,4-dihydropyridine;

6-methyl-3,5-dicarboethoxy-4-(o-nitrophenyl)-2-phenylthiomethyl-1,4-dihydropyridine;

6-methyl-3,5-dicarboethoxy-4-(m-nitrophenyl)-2-[(p-methoxyphenyl)-thiomethyl]-1,4-dihydropyridine;

6-methyl-3,5-dicarboethoxy-4-(m-nitrophenyl)-2-[(p-acetamidophenyl)-thiomethyl]-1,4-dihydropyridine;

6-methyl-3,5-dicarboethoxy-4-(m-nitrophenyl)-2-[(p-aminophenyl)-thiomethyl]-1,4-dihydropyridine;

6-methyl-5-cyano-3-carboethoxy-4-(m-nitrophenyl)-6-[(p-chlorophenyl)-thiomethyl]-1,4-dihydropyridine;

6-methyl-3,5-dicarboethoxy-4-(m-nitrophenyl)-2-[(1-methylimidazol-2-yl)-thiomethyl]-1,4-dihydropyridine;

6-methyl-3,5-dicarboethoxy-4-(m-nitrophenyl)-2-[(4-phenoxymethyl-5-carboethoxy-imidazol-2-yl)-thiomethyl]-1,4-dihydropyridine;

6-methyl-3,5-carboethoxy-4-(m-nitrophenyl)-2-(2,3-dihydroxypropylthio)-methyl-1,4-dihydropyridine;

6-methyl-3,5-dicarboethoxy-4-(m-nitrophenyl)-2-(3-isopropylamino-2-hydroxypropylthio)-methyl-1,4-dihydrophrine;

6-methyl-3,5-dicarboethoxy-4-(m-nitrophenyl)-2-(2-amino-2-carboethoxy-ethylthio)-methyl-1,4-dihydropyridine;

2-(p-fluorophenylthio)methyl-3,5-dicarboethoxy-4-(m-nitrophenyl)-6-methyl-1,4-dihydropyridine;

6-methyl-3,5-dicarboethoxy-4-(m-nitrophenyl)-2-(2-acetamidoethylthio)-methyl-1,4-dihydropyridine;

6-methyl-3,5-dicarboethoxy-4-(m-nitrophenyl)-2-acetylthiomethyl-1,4-dihydropyridine;

6-methyl-3,5-dicarboethoxy-4-(m-nitrophenyl)-2-mercaptomethyl-1,4-dihydropyridine;

S-[(6-methyl-3,5-dicarboethoxy-4-(m-nitrophenyl)-1,4-dihydropyridin-2-yl)-methyl]-isothiouronium chloride;

6-methyl-3,5-dicarboethoxy-4-(m-nitrophenyl)-2-[(p-methoxyphenyl)-sulphinyl]-methyl-1,4-dihydropyridine;

6-methyl-3,5-dicarboethoxy-4-(m-nitrophenyl)-2-[(p-fluorophenyl)-sulphinylmethyl]-1,4-dihydropyridine;

6-methyl-3,5-dicarboethoxy-4-(m-nitrophenyl)-2-[(4-phenoxymethyl-5-carboethoxy-imidazol-2-yl)-sulphinyl]-methyl-1,4-dihydropyridine;

2-methyl-3-nitro-5-carboethoxy-4-(m-nitrophenyl)-6-(butylthio)-methyl-1,4-dihydropyridine;

2-methyl-3-nitro-5-carboethoxy-4-(m-nitrophenyl)-6-(2,3-dihydroxypropylthio)-methyl-1,4-dihydropyridine;

6-methyl-3,5-dicarboethoxy-4-(m-nitrophenyl)-2-(2-aminoethylsulphinyl)-methyl-1,4-dihydropyridine;

6-methyl-3,5-dicarboethoxy-4-(m-nitrophenyl)-2-(2-amino-2-carboethoxyethylsulphonyl)-methyl-1,4-dihydropyridine;

2-(2-aminoethylthio)methyl-3,5-dicarboethoxy-4-(m-nitrophenyl)-6-methyl-1,4-dihydropyridine;

2-(2-aminoethylthio)methyl-3-carboethoxy-5-carbomethoxy-4-(m-nitrophenyl)-6-methyl-1,4-dihydropyridine; and its fumarate and maleate salts;

2-(2-aminoethylthio)methyl-3-carboethoxy-5-carbomethoxy-4-(m-chloro-phenyl)-6-methyl-1,4-dihydropyridine;

2-(2-aminoethylthio)methyl-3-carboethoxy-5-carboisopropoxy-4-(m-nitrophenyl)-6-methyl-1,4-dihydropyridine;

2-(2-aminoethylthio)methyl-3-carboethoxy-5-carbomethoxy-4-(m-trifluoromethylphenyl)-6-methyl-1,4-dihydropyridine;

2-(2-aminoethylthio)methyl-3-carboethoxy-5-carbomethoxy-4-phenyl-6-methyl-1,4-dihydropyridine;

2-(2-aminoethylthio)methyl-3-carboethoxy-5-carboterbutoxy-4-(m-nitrophenyl)-6-methyl-1,4-dihydropyridine;

2-(2-aminoethylthio)methyl-3-carboethoxy-5-methoxyethoxycarbonyl-4-(m-nitrophenyl)-6-methyl-1,4-dihydropyridine;

2-(2-aminoethylthio)methyl-3-carboethoxy-5-[2-(N-methyl-N-benzylamino)ethox]carbonyl-4-(m-nitrophenyl)6-methyl-1,4-dihydropyridine;

2-(3-aminopropylthio)methyl-3-carboethoxy-5-carbomethoxy-4-(m-nitrophenyl)-6-methyl-1,4-dihydropyridine;

2-(4-aminobutylthio)methyl-3-carboethoxy-5-carbomethoxy-4-(m-nitrophenyl)-6-methyl-1,4-dihydropyridine;

2-(2-aminopropylthio)methyl-3-carboethoxy-5-carbomethoxy-4-(m-nitrophenyl)-6-methyl-1,4-dihydropyridine;

2-(2-N-methylaminoethylthio)methyl-3-carboethoxy-5-carbomethoxy-4-(m-nitrophenyl)-6-methyl-1,4-dihydropyridine;

2-(2-N-isopropylaminoethylthio)methyl-3-carboethoxy-5-carbomethoxy-4-(m-nitrophenyl)-6-methyl-1,4-dihydropyridine;

2-(2-N-n-butylaminoethylthio)methyl-3,5-dicarboethoxy-4-(m-nitrophenyl)-6-methyl-1,4-dihydropyridine;

2-(2-N-n-butylaminoethylthio)methyl-3-carboethoxy-5-carbomethoxy-4-(m-nitrophenyl)-6-methyl-1,4-dihydropyridine;

2-(2-N-benzylaminoethylthio)methyl-3,5-dicarboethoxy-4-(m-nitrophenyl)-6-methyl-1,4-dihydropyridine;

2-[2-N-(2-hydroxy-3-N-morpholinomethyl-5-methoxybenzyl)-aminoethylthio]methyl-3,5-dicarboethoxy-4-(m)nitrophenyl)-6-methyl-1,4-dihydropyridine;

2-(2-N,N-dimethylaminoethylthio)methyl-3,5-dicarboethoxy-4-(m-nitrophenyl)-6-methyl-1,4-dihydropyridine;

2-(2-aminoethylsulphinyl)methyl-3-carboethoxy-5-carbomethoxy-4-(m-nitrophenyl)-6-methyl-1,4-dihydropyridine;

2-(3-pyridylmethylthio)methyl-3,5-dicarboethoxy-4-(m-nitrophenyl)-6-methyl-1,4-dihydropyridine;

2-(5-amino-1,3,4-thiadiazol-2-yl)thiomethyl-3,5-dicarboethoxy-4-(m-nitrophenyl)-6-methyl-1,4-dihydropyridine;

2-(5-amino-1,2,4-triazol-3-yl)thiomethyl-3,5-dicarboethoxy-4-(m-nitrophenyl)-6-methyl-1,4-dihydropyridine;

2-(carboethoxymethylthio)methyl-3,5-dicarboethoxy-4-(m-nitrophenyl)-6-methyl-1,4-dihydropyridine;

2-(2-cyanoethylthio)methyl-3,5-dicarboethoxy--4-(m-nitrophenyl)-6-methyl-1,4-dihydropyridine;

2-(cyanomethylthio)methyl-3,5-dicarboethoxy-4-(o-chlorophenyl)-6-methyl-1,4-dihydropyridine;

2-(2-oxopropylthio)methyl-3-carboethoxy-5-carbomethoxy-4-(m-nitrophenyl)-6-methyl-1,4-dihydropyridine;

2-(2-phenyl-2-oxo-ethylthio)methyl-3,5-dicarboethoxy-4-(m-nitrophenyl)-6-methyl-1,4-dihydropyridine;

2-[2-(4-imidazol-1-yl)phenyl-2-oxoethylthio]methyl-3,5-dicarboethoxy-4-(m-trifluoromethylphenyl)-6-methyl-1,4-dihydropyridine;

2-(2,2-diethoxyethylthio)methyl-3-carboethoxy-5-carbomethoxy-4-(m-trifluoromethylphenyl)-6-methyl-1,4-dihydropyridine;

2-(oxiran-2-ylmethylthio)methyl-3,5-dicarboethoxy-4-(m-nitrophenyl)-6-methyl-1,4-dihydropyridine;

2-(oxiran-2-ylmethylthio)methyl-3,5-dicarboethoxy-4-(m-chlorophenyl)-6-methyl-1,4-dihydropyridine;

2-[(pyrrolidin-2-yl)methylthio]methyl-3-carboethoxy-5-carbomethoxy-4-(m-nitrophenyl)-6-methyl-1,4-dihydropyridine, enantiomers, diastereomers and diastereomeric mixtures thereof.

The compounds of the inventions are prepared by a process comprising: a) reacting a compound of formula II

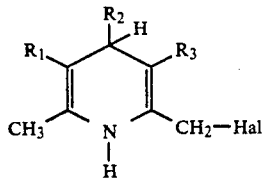

wherein $R_1$, $R_2$, $R_3$ are as defined above and Hal is chlorine, bromine, iodine, with a thiol of formula III $$R'_4 SH \quad (III)$$

wherein $R'_4$ is hydrogen, $C_2$-$C_{12}$ alkanoyl, —C(=NR$_8$)NR$_9$R$_{10}$ or R$_4$ being R$_4$, R$_8$, R$_9$ and R$_{10}$ as defined above, so obtaining a compound of formula I wherein $\phi$ is a thiol or its $C_2$-$C_{12}$ alkanoylester, a thiouronium salt —S—C(N=R$_8$)NR$_9$R$_{10}$/(+)Hal(−) or —S(O)$_n$R$_4$ (R$_4$, R$_8$, R$_9$, R$_{10}$, Hal are as defined above and n is zero) which may be optionally oxidized to give a compound of formula I wherein n is 1 or 2 and, if necessary, after removal of the known protecting groups, possibly present in R$_4$, converting a compound of formula (I) into another compound of formula (I), and/or, if desired, salifying a compound of formula (I) and/or, if desired, obtaining a free compound of formula (I) from a salt thereof and/or, if desired, separating a mixture of isomers into the single isomers;

b) reacting a compound of formula Ia

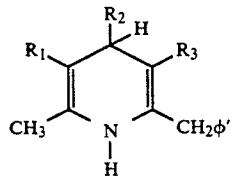

wherein $R_1$, $R_2$, $R_3$ are as defined above and $\phi'$ is a member selected from the group consisting of a thiol and of a masked thiol group such as thio-$C_2$-$C_{12}$ alkanoylester or a thiouronium salt —S—(C=NR$_8$)NR$_9$R$_{10}$/(+)Y$^-$ with a compound of formula IV $$R_4—M \quad (IV)$$

wherein $R_4$ is as defined above and M is a known leaving group such as chlorine, bromine, iodine, trifluoroacetate, trifluoromethanesulphonate, an alkyl or an arylsulphonate, to give a compound of formula I wherein $\phi$ is —S(O)$_n$R$_4$ being $R_4$ as defined above and n is zero, which may be optionally oxidized to give a compound of formula I wherein n is 1 or 2 and, if necessary, after removal of the known protecting group, possibly present in R$_4$, converting a compound of formula (I) into another compound of formula (I) and/or, if desired, salifying a compound of formula (I) and/or, if desired, obtaining a free compound of formula (I) from a salt thereof and/or, if desired, separating a mixture of isomers into the single isomers;

c) reacting a compound of general formula V $$CH_2=CH—R''_4 \quad (V)$$

wherein $R''_4$ is a member selected from the group consisting of cyano, alkoxycarbonyl, —CONR$_6$R$_7$, CO—(CH$_2$)$_p$—B wherein R$_6$, R$_7$, B and p, are as defined above, with a compound of formula Ia to give a compound of formula Ib

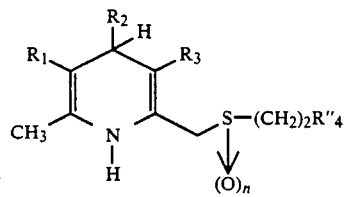

wherein $R_1$, $R_2$, $R_3$, $R''_4$, are as above defined and n is zero, which may be, if desired, oxidized to give a compound of formula Ib wherein n is 1 or 2 and, if necessary, converting a compound of formula Ib in another compound of formula I and/or, if desired, separating a mixture of isomers into the single isomers;

d) cyclizing a compound of formula VI

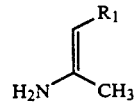

wherein $R_1$ is as above defined, with an alkylidene compound of formula VII

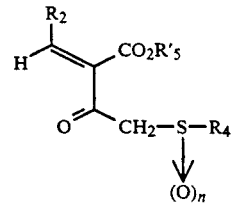

wherein $R_2$, $R_4$ and n are as defined above and $R'_5$ is a substituted or an unsubstituted $C_1$-$C_6$ alkyl chain, a $C_3$-$C_6$ alkenyl chain, an unsubstituted or substitued aryl or $C_1$-$C_4$ aralkyl, to give a compound of formula Ic

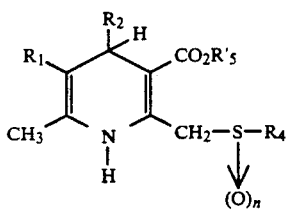

(Ic)

wherein $R_1$, $R_2$, $R'_5$, $R_4$ and n are as defined above and, if desired, after removal of the known protecting group possibly present in $R_4$, converting a compound of formula I in another compound of formula I and/or, if desired, salifying a compound of formula I and/or, if desired, obtaining a free compound of formula (I) from a salt thereof and/or, if desired, separating a mixture of isomers into the single isomers;

e) reducing a compound of formula Id

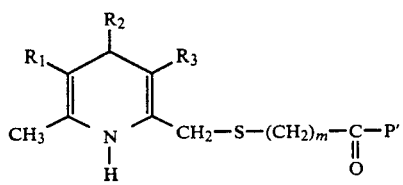

(Id)

wherein $R_1$, $R_2$, $R_3$, m are as above defined and P' is hydrogen or $C_1$-$C_8$ alkyl, $(CH_2)_{p1}$, —W, with a borohydride and/or a cyanoborohydride of an alkaline metal or of a quaternary ammonium salt, in the presence of an ammonium salt of formula VIII $$H_2NP'_1P'_2 \quad (VIII)$$

wherein each of $P'_1$ and $P'_2$, which are the same or different, may be hydrogen, $C_1$-$C_6$ alkyl, $(CH_2)_{p1}$—W or, taken together with the nitrogen atom to which they are linked, form the residue

and $p_1$, W and X are as defined above, to give a compound of formula Ie

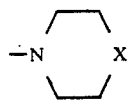

(Ie)

wherein $R_1$, $R_2$, $R_3$, P, $P'_1$, $P'_2$ and m are as above defined, which may be transformed in another compound of formula I by oxidation of the sulphur atom or by salification or by optical resolution;

f) reducing an ammonium salt of formula Ig

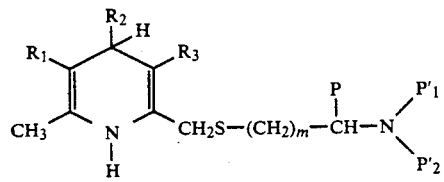

(Ig)

wherein $R_1$, $R_2$, $R_3$, m, $P'_2$ are as above defined and r is an integer from 3 to 4 and $Y^-$ is a monovalent anion, by reaction with an alkaline or quaternary ammonium salt of a borohydride and/or a cyanoborohydride to give a compound of formula Ih

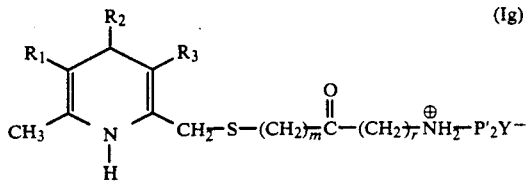

(Ih)

wherein $R_1$, $R_2$, $R_3$, m, r and $P'_2$ are as above defined, which, if desired, may be optionally subjected to separation of the diastereoisomers;

g) cleavaging an oxirane ring of a compound of formula (Ii)

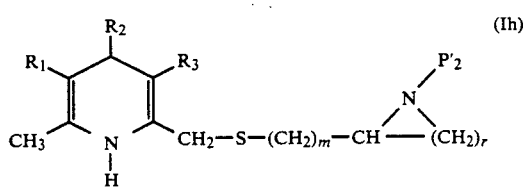

(Ii)

wherein $R_1$, $R_2$, $R_3$, B, n, $n_1$ and p are as defined above, with a nucleophilic compound selected from the group consisting of water, $C_1$-$C_3$ lower alcohols, $C_1$-$C_3$ lower alkylthiols, ammonia, a monoalkyl or a dialkylamine, to give a compound of formula (Il)

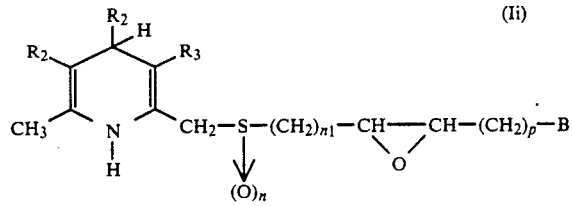

(Il)

wherein $R_1$, $R_2$, $R_3$, B, n, $n_1$ and p are as above defined and one of $R_{11}$ and $R_{12}$ is hydroxy and the other may be hydroxy, —$NH_2$, $C_1$-$C_3$ alkoxy, $C_1$-$C_3$ alkylthio, a monoalkyl or a dialkylamine.

Both the process of the invention comprising the reaction of a compound of formula II with a thiol of formula III to produce a compound of formula I and the process converting a thiol or a masked thiol of formula Ia in another compound of formula I, wherein φ is-$SR_4$, by treatment with a reagent of formula IV, represent an usual method pursued in the art for introducing thiols and thioether groups in an organic substrate.

The process may be respectively performed by reaction with either stoichiometric amounts or a small excess of the reagents of formula III and of formula IV in a solvent, miscible or immiscible with water, in homogeneous or in heterogeneous phase or in phase-transfer conditions, in the presence of a base in equimolar amounts or in excess.

Suitable solvents are $C_1$-$C_5$ alcohols; amides such as formamide, dimethylformamide, dimethylacetamide; cyclic or linears ethers such as dimethoxyethane, dioxane, tetrahydrofuran, dimethylsulphoxide, ketones and acetales such as acetone, butanone, methylale; esters such as ethylacetate, ethylformiate; halogenated hydrocarbons such as $CCl_4$, $CH_2Cl_2$, 1,2-dichloroethane; aliphatic hydrocarbons such as n-hexane, n-heptane; cycloaliphatic hydrocarbons such as cyclohexane; aromatic hydrocarbons such as benzene, toluene, pyridine, as well as mixtures thereof.

The reaction may be carried out at temperatures ranging from about $-30°$ C. to about $100°$ C.; preferably from about $-15°$ C. to about $60°$ C. and more preferably from $0°$ C. to room temperature.

The reaction times range from few minutes to two days, but usually do not exceed two hours when it is carried out at room temperature.

Preferred bases may be an inorganic base, e.g., an alkaline or an alkaline-earth hydroxide, carbonate, bicarbonate, hydride, amide e.g. NaOH, $K_2CO_3$, $Na_2CO_3$, $Li_2CO_3$, $KHCO_3$, MeONa, EtONa, ter-buOK, $(EtO)_2Mg$, $CaH_2$, NaH, $NaNH_2$; or an organic base such as alkylamine e.g. isopropylamine, cyclohexylamine, butylamine, triethylamine, or an aromatic base e.g. pyridine or an alkylsubstituted pyridine or cyclic amines e.g. N-methyl-piperidine and 1,4-diazabicyclo[2,2,2]octane.

The reaction of a compound of formula VII with a compound of formula V is carried out with an excess of the compound of formula V e.g. at least 1.1 molar equivalents per mole of the compound of formula III preferably in presence of tetramethylguanidine as a catalyst, in inert solvents e.g. esters, halogenated hydrocarbons, linear or cyclic ethers or aromatic hydrocarbons, $C_1$-$C_5$ alcohols preferably at room temperature.

The thioether bond of a compound I may be selectively oxidized to give a sulphoxide or a sulphone, according to known methods. Selective oxidation of a sulphide to sulphoxide may be performed using one molar equivalent of an organic peracid such as perbenzoic, m-Cl-perbenzoic, monoperphtalic, peracetic, performic and peroxytrifluoroacetic acid or using periodic acid or a salt thereof. Two molar equivalents or an excess of a peracid mentioned above are used for obtaining the corresponding sulphones starting from a sulphide of formula I (n=0), and one molar equivalent is necessary for the conversion of a compound of formula I (n=0) into a compound of formula I (n=2).

Suitable solvents are those which are inert to the oxidizing reagent; the reaction may be performed in the presence of an insoluble inorganic base such as $Na_2CO_3$, $KHCO_3$, $NaHCO_3$ in order to remove the reduced acid from the reaction mixture; preferably the reaction is carried out at temperatures ranging from $0°$ C. to room temperature and the reaction times range from few minutes to a few hours. The 1,4-dihydropyridine ring is not oxidized to pyridine ring under said reaction conditions.

The cyclization of a compound of formula VI with a compound of formula VII to give a compound of formula Ic may be carried out by reaction with either stoichiometric amount or a small excess of the enamine VI in inert solvents such as benzene, toluene, tetrahydrofuran, $CH_2Cl_2$, $CHCl_3$, 1,2-dichloroethane, pyridine, acetic acid, $C_1$-$C_5$ lower alcohols; or mixture thereof.

The reaction is preferably carried out at temperatures ranging from room temperature to the reflux temperature of the reaction mixture; the reaction is preferably carried out in a temperature range from $45°$ to $80°$ C.; as a consequence, the reaction times may vary from several days to few hours, but usually do not exceed four hours.

A reduction of the reaction time may be achieved by addition of catalytic amount of an inorganic or organic acid e.g. hydrochloric, p-toluensulphonic or acetic acid, to the cooled reaction mixture after 2–3 hours heating.

Preferred compounds of the invention are compounds of formula (I) having a mono- or polysubstituted thioether group. Particularly preferred substituents are hydroxy, amino, carbonyl, carboxyl, epoxy groups, which may be optionally protected with protective groups removable selectively and under mild reaction conditions.

Known protective groups are, for example, acetalethers, emolethers, silylethers for alcoholic and phenolic groups, amide and 3,5-dimethylpyrrol for primary amines, acetals and ketals for carbonyl compounds, ter-butyl and alkoxymethylester for carboxylic acids; all said protective groups may be removed easily by acid hydrolysis.

Cyclic imides may be used to protect primary amino groups and their removal may be easily carried out by treatment with hydrazines or other amines e.g. butylamine.

Analogously, isothiouronium salts and alkanoylthioesters may also be used to protect thiol groups; their removal is easily carried out by treatment with ammonia or lower alkyl amines. It should be understood that functional groups such as amino, hydroxy, carbonyl, thiol, carboxyl optionally present in $R_4$, $R'_4$, $R''_4$ groups in the compounds of formula III, IV, V and VII, may be present either in free or protected form: in the latter case, they may be deprotected in any convenient step of the synthetic process.

On the other hand, free amino, hydroxy, thiol, carboxylic groups optionally present in the compounds of formula I, may be optionally converted into amides, Schiff bases, esters, silyl derivatives to make the purification process of the final compounds easier.

On the other hand, using methods well-known in the art, reduction (for example with alkaline borohydride or cyanoborohydride or with their tetraalkylammonium salts) of Schiff bases yields secondary amino groups, while reduction of esters of $\alpha$-aminoacid yields $\alpha$-aminoalcohols, intermediates for 5-dihydrooxazol-2-ones. Similarly, vicinaldiols, if present in $R_4$, may be converted into epoxides, via monoalkyl(aryl)sulphonates, the epoxide may be cleaved to produce for example $\alpha$-hydroxy-alkylamines, $\alpha$-hydroxyalkylthiols, $\alpha$-hydroxyether (or thioethers).

Finally, reductive amination may be used to convert a carbonyl compound of formula Id into an amino compound of formula Ie. Particularly preferred reductive amination is that of a salt of a bifunctional $\gamma$- (or $\delta$)-aminoketone of formula Ig into cyclic amine of formula Ih.

The starting materials of formula III, IV, V, VI are known compounds, commercially available and/or easily preparable with known methods.

The 2-halomethyl-1,4-dihydropyridines of formula II are described in the italian Pat. Appln. No. 21875 A/85 (6.8.1985) in the applicant's name.

The compounds of formula VII are prepared by reaction of an aldehyde of formula VIII $$R_2CHO \qquad (VIII)$$

with a β-ketoester of formula IX

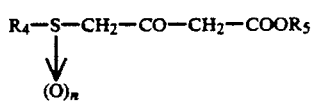

(IX)

When the β-ketoesters of formula IX are unknown compounds, they may be prepared using known methods starting from the known acids of formula X

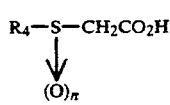

(X)

An activated form of acid of formula X (e.g. chloride, imidazolide) may be reacted with Meldrum acid or with the magnesium enolate of a malonic acid emiester. For more detailed illustrations of general methods for β-ketoester synthesis see for ex. Y. Oikawa et al., J. Org. Chem. 43, 2087 (1978), D.G. Melillo et al., Tetrah. Lett. 21, 2783 (1980) and D.C. Brooks et al., Angew. Chem. Int. Ed., 18, 72 (1979).

The compounds of the invention of formula I protect cellular membranes form oxidative injuries; a reduced malondialdehyde formation is observed after incubation of rat erithrocyte membranes (M. Aishita et al., Arch. Intern. Pharmacodyn. 261, 316, 1983) and of rat brain homogeneate (Stocks et al., Clin. Sci. Molec. Med., 47, 215, 1974) with the compounds of the invention.

Sudden death induced by bolus of arachidonic acid or of a mixture of ADP and collagene in mice and rabbits is prevented by previous oral and/or intraperitoneal treatment with the compounds of formula I.

The compounds of the invention were tested, according to the Godfraind's procedure (T. Godfraind et al., Arch. Intern. Pharmacol., 172, 235, 1968), to evaluate their property of inhibiting the contraction induced by $CaCl_2$ in $K^+$-depolarized aorta strips, in comparison to nifedipine.

Many compounds of the invention showed $ID_{50}$ ranging from $10^{-7}$ to $10^{-10}$ (nifedipine, $ID_{50}2.7.10^{-8}$).

The antihypertensive activity of the compounds of the invention was also tested, at different times, after oral administration to conscious spontaneously hypertensive rats (SH rats), measuring the decrease of the mean blood pressure (B.P.).

Some compounds of the invention induce a 15% decrease at least, of the basal values of the mean B.P. when administered at a dose level lower than 1/10 of the corresponding $LD_{50}$.

A 15% decrease of the mean B.P. is generally considered to be a predictive indication for a significant cardiovascular activity.

It is to be pointed out that a satisfactory correlation is not often observed between the calcium antagonist potency, as measured by "in vitro" test, and the antihypertensive activity shown "in vivo" by some compounds of the present inventions.

Representative examples are reported in the following table:

| Substance 6-methyl-3,5-dicarboethoxy-4-(m-nitrophenyl)-1,4-dihydropyridine | $ID_{50}$ (M) aorta contractility inhibition | Decrease of the mean blood pressure in SH Rats | |
|---|---|---|---|
| | | mmHg | doses mg/kg/os |
| 2-methyl-isothiouronium hydrochloride | $2.2 \cdot 10^{-7}$ | 45 | 3.1 |
| 2-(2,3-dihydroxypropyl)-thiomethyl | $2.2 \cdot 10^{-8}$ | 38 | 12.5 |
| 2-(acetylaminoethyl)-thiomethyl | $9.2 \cdot 10^{-9}$ | 26 | 3.1 |
| 2-(2-hydroxyethyl)-thiomethyl | $5 \cdot 10^{-8}$ | 0-5 | 3.1 |
| 2-(2-cyanoethyl)-thiomethyl | $5 \cdot 10^{-8}$ | 0-5 | 6.2 |
| 2-(2-ethoxycarbonyl-2-amino-ethyl)-thiomethyl | $6 \cdot 10^{-8}$ | 30 | 3.1 |
| 2-(p-methoxyphenyl)-thiomethyl | $9 \cdot 10^{-8}$ | 35 | 12 |
| 2-(p-methoxyphenyl)-sulphynylmethyl | $10^{-6} - 10^{-7}$ | 51 | 12 |
| 2-(p-fluorophenyl)-thiomethyl | $10^{-6}$ | 29 | 12.5 |
| 2-(p-fluorophenyl)-sulphynylmethyl | $8 \cdot 10^{-8}$ | 40 | 12.5 |
| 2-(p-aminophenyl)-thiomethyl | $8.4 \cdot 10^{-8}$ | 25 | 6.25 |
| 2-(5-amino-1,3,4-thiazol-2-yl)thiomethyl | $\leq 10^{-6}$ | 68* | 12 |
| 2-(5-amino-1,3,4-thiadiazol-2-yl)-thiomethyl | $10^{-6} \div 10^{-7}$ | 67* | 12 |
| 2-hydroxy-propyl)-thiomethyl | $8 \cdot 10^{-10}$ | 5-12 | 3.1 |
| 2-acetylthiomethyl | $2.5 \cdot 10^{-8}$ | 20 | 6 |

*Long lasting activity.

The activity of the compounds of the invention on the gastrointestinal tract was also studied in order to assess a) cytoprotective action against lesions induced by NSAI drugs; b) ability to prevent the ulcers induced by the method of Togagi-Okabe (Japan J. Pharmacol. 18, 9, 1968).

2-(3,2-Dihydropropyl)thiomethyl-6-methyl-3,5-dicarboethoxy-4-(m-nitrophenyl)-1,4-dihydropyridine is a representative compound of the invention having an $ED_{50}$ lower than 1 mg/kg by oral administration.

The compounds of the invention are moreover useful for the control of electrolyte fluxes through membranes of blood cellular components such as platelets, leucocytes, eritrocytes and for the regulation of their deformability and reactivity against excitatory stimuli. At the cellular level, they are also useful in the control of enzymatic processes involving both activation and inhibition of calcium-dependent enzymes.

The compounds of the invention are consequently considered useful as vasodilators and hypotensive agents for the treatment of thromboembolic diseases, for treatment of myocardial, renal and cerebral ischemias. The compounds I are also particularly useful as cytoprotective and antiulcer agents at gastric level.

Dose order of 0.01 to 10 mg/kg/die and preferably ranging from 0.05 and 5 mg/kg/die can be given 1 to 2-3 times a day, the exact dose depending on the age, weight and condition of the patient and on the administration route. A dose for oral administration may comprise, for example, from 0.05 to 70 mg of active principle.

The amount for parenteral route may vary from 0.001 to 5 mg/kg/die, preferably from 0.01 to 2 mg/kg/die.

Some monosubstituted aminoalkylthiomethyl compounds of the invention, such as 2-aminoethylthio-4-(m-nitrophenyl)-3,5-diethoxycarbonyl-6-methyl-1,4-dihydropyridine show peculiar properties such as a pronounced and long lasting antihypertensive activity at very low doses (for example 0.4 mg/kg/os) when tested in conscious SH rats and in conscious DOCA-rats (i.e. rats made hypertensive by treatment with desoxycorticosterone acetate) by oral route.

Other typical monofunctionalized compounds of the invention are for example: 2-[(2-aminoethyl)thio]methyl-3-carboethoxy-5-carbomethoxy-4-m-nitrophenyl-6-methyl-1,4-dihydropyridine and the corresponding: 4-o-chlorophenyl, 4-m-trifluoromethyl-phenyl, 4-m-chloro-phenyl derivatives; 2-[(2-aminoethyl)thio]methyl-3-carboethoxy-5-carboisopropoxy-4-m-nitrophenyl-6-methyl-1,4-dihydropiridine hydrochloride; 2-[(2-N-butylaminoethyl)thio]methyl-3,5-dicarboethoxy-4-m-nitrophenyl-6-methyl-1,4-dihydropyridine and the corresponding N-methyl and N-isopropyl derivatives; 2[(2-aminopropyl)thio]methyl-3-carboethoxy-5-carbomethoxy-4-m-nitrophenyl-6-methyl-1,4-dihydropyridine and the 2-[(4-aminobutyl)thio]methyl derivatives, and salts thereof.

The antihypertensive effect is strictly dose dependent in the investigated dosage range from 1.5 to 0.1 mg/kg/os. The maximum hypotensive effect, proportional to the administered dose, takes place 6–7 hours after the administration and the blood pressure is maintained at the decreased level for other 4–5 hours, at least.

The gradual onset of the antihypertensive effect is not coupled with reflex tachycardia, which is often observed after treatment with other antihypertensive agents such as, for example, hydralazine and many dihydropyridines, in the same experimental models.

On the contrary, no substantial modifications of the mean B.P. and heart rate are observed in normal conscious rat after oral administration of these monofunctionalized aminoalkylthiomethyl-1,4-dihydropyridines at the same dose range level (1.5–0.1 mg/kg). It should be pointed out that the same compounds, investigated "in vitro", show modest to middle inhibitory properties against $CaCl_2$-induced contraction of $K^+$-depolarized rat aorta strips with calculated $ID_{50}$ ranging from $10^{-6}$ to $10^{-7}$ M. Only after prolongation of the contact time of solutions of these compounds with the tissue preparations from the standard 2–5 minutes to 2–3 hours before the $CaCl_2$ stimulated contractions, it is possible to calculate $ID_{50}$ ranging from $10^{-8}$ to $10^{-10}$ M.

The peculiar antihypertensive effect, its gradual onset, the long lasting activity lead to suppose that the compounds of formula I and more precisely those of formula Ih, Ie wherein $R_1$ is a carboxyester group, are more specifically useful in human and veterinary therapy for treatment of hypertensive diseases of different cause and severity.

For the achievement of the desired effects in human and veterinary therapy, these compounds of formula Ie, Ih, of the invention, may be administered by oral route or by parenteral route in a variety of dosage forms e.g. orally in the form of tablets capsules or liquids; rectally in the form of suppositories, subcutaneously, intramuscularly, or intravenously administration or by infusion in emergency situation.

The amounts of active ingredient may range from 1 $\mu$g to 1 mg/kg/die preferably from 1 $\mu$g to 0.1 mg/kg/die by oral administration. The parenteral dosage may range from 0.1 $\mu$ to 0.5 mg/kg/die and preferably from 0.5 $\mu$g to 0.2 mg/kg/die. One dose for oral administration may contain, for example, from 50 $\mu$g to 5 mg of active ingredient.

The compounds of the invention may be administered once a day, even if administrations more or less frequent may be sometimes convenient according to the age, weight and patient's condition and to the administration route.

Suitable pharmaceutical formulation may be prepared according to conventional techniques such as those described in Remington's Pharmaceutical Sciences Handbook", Hack Publishing Co., U.S.A.

For the oral administration, the compound may be formulated in solid or liquid preparations such as capsules, pills, tablets, powders, solutions, suspensions or emulsions. The unit dosage form may be the hard or soft gelatine capsule containing for instance lubricants and inert excipients such as lactose, saccharose or starch. Alternatively, the compounds of the invention may be administered as tablets, on carriers such as lactose, saccharose or starch in combination with binders such as starch itself or gelatin, disintegrating agents such as potato starch, or alginic acid, and lubricants such as stearic acid and magnesium stearate.

For parenteral administration the compounds of the invention may be administered in injectable forms, dissolved or suspended in pharmaceutically acceptable diluents, with a pharmaceutical carrier such as a sterile liquid such as water or an oil, with or without the addition of other pharmaceutically acceptable excipients. Oils which may be used in said preparations are of mineral, vegetal, animal or synthetic kind. Generally, as a carrier for injectable solutions the following substances may be used: water, salts, aqueous solutions, dextrose or other sugars aqueous solutions, ethanol, glycols such as propylenglycol and polyethylenglycols.

For the rectal administration, the compounds may be formulated in forms of suppositories, mixed with conventional vehicles such as, for example, cocoa butter, wax, polyvinylpyrrolidone or polyoxyethyleneglycols, or derivatives thereof.

The administration route generally preferred is the oral route, while the preferred pharmaceutical formulations are capsules.

The invention is illustrated by the following non limitative examples, wherein the abbreviations "DME", "Et$_2$O", "AcOEt", "EtOH", "TEA", "AcOH", "THF", "MeOH" refer to 1,2-dimethoxyethane, diethylether, ethylacetate, ethanol, triethylamine, tetrahydrofurane and methanol, respectively.

EXAMPLE 1

A stirred ethanolic solution (200 ml) of an alkaline alkoxide, for example sodium ethoxide (20 g), is saturated, at $+10°$ C., with dry hydrogen sulfide, cooled to $-15°$ C., and added with a solution of 2-chloromethyl-3,5-dicarboethoxy-4-(m-nitrophenyl)-6-methyl-1,4-dihydropyridine (25 g) in DME (70 ml). After one hour, the reaction mixture is warmed to 0° C., acidified with $H_2SO_4$ (10% water solution; 100 ml) and diluted with water (1400 ml). The precipitate is filtered off, dried in vacuum, and recrystallized from Et$_2$O to give 23 g of 2-mercaptomethyl-3,5-dicarboethyxy-4-(m-nitrophenyl)-6-methyl-1,4-dihydropyridine, m.p. 145°–147° C.

EXAMPLE 2

A solution of 2-chloromethyl-3,5-dicarboethoxy-4-(m-nitrophenyl)-6-methyl-1,4-dihydropyridine (1 g) and tetrabutylammonium hydrogen sulfide (0.7 g) in methylene chloride (10 ml) is stirred at −10° C., for 20 minutes, neutralized with a drop of AcOH, evaporated under vacuum and the residue recrystallized from $Et_2O$ to give 0.7 g of 2-mercaptomethyl-3,5-dicarboetoxy-4-(m-nitrophenyl)-6-methyl-1,4-dihydropyridine, m.p. 145°–147° C.

EXAMPLE 3

Potassium thioacetate (1.5 g) is added, at 10° C. under $N_2$ atmosphere, to a stirred solution of 2-chloromethyl-3-carboethoxy-5-cyano-4-(m-nitrophenyl)-6-methyl-1,4-dihydropyridine (5 g) in acetone (50 ml). After 20 minutes the reaction mixture is evaporated to dryness and the residue is partitioned between AcOEt (80 ml) and water (30 ml).

The organic layer is washed with water (2×20 ml), dried on $Na_2SO_4$ and the solvent is evaporated under vacuum. The residue is recrystallized from $Et_2O$ to give 4.9 g of 2-(acetylthio)methyl-3-carboethoxy-5-cyano-4-(m-nitrophenyl)-6-methyl-1,4-dihydropyridine, m.p. 155°157° C.

A water solution of $NH_3$ (28%, 5.3 ml) is added at 0° C. under $N_2$ atmosphere to a stirred solution of the above described compound (2 g) in DME (20 ml).

After 30 minutes the solution is diluted with ice water (100 ml) and extracted with $Et_2O$ (3×30 ml) to give, after the usual work-up, 1.5 g of 2-mercaptomethyl-3-carboethoxy-5-cyano-4-(m-nitrophenyl)-6-methyl-1,4-dihydropyridine, oil.

NHR $CDCl_3$): δ(TMS): 1.10–1.20 (3H, t), 1.80–2.00 (1H, t); 2.20 (3H, s); 4.00–4.40 (4H, m); 5.10 (1H, s); 7.00–8.20 (5H, m).

EXAMPLE 4

A mixture of 2-chloromethyl-3,5-dicarboethoxy-4-(m-nitrophenyl)-6-methyl-1,4-dihydropyridine (6 g) and thiourea (1.2 g) in EtOH (60 ml) is refluxed for 3 hours; after cooling to room temperature, the crystalline precipitate is filtered off to give 4.8 g of S-[(6-methyl-3,5-dicarboethoxy-4-(m-nitrophenyl)-1,4-dihydropyridin-2-yl)methyl]-isothiouronium hydrochloride, m.p. 219°–220° C.

The free isothiourea, as an oil, is prepared by treatment of a suspension of the isothiouronium salt (for example 1 g) in AcOEt (20 ml) with aqueous saturated $NaHCO_3$ solution (2×10 ml). The organic phase is washed with water, dried on $Na_2SO_4$ and evaporated to dryness.

By subsequent treatment of a solution of the free base in a suitable solvent (for example AcOEt) with a solution of equimolar amounts of an acid (for example fumaric and acetic acid) the corresponding isothiouronium salts: fumarate (m.p. 82°–85° C.) and acetate (m.p. 69°–70° C.) are obtained.

A solution of a isothiouronium salt (for example the hydrochloride 4.7 g) and n-propylamine (0.7 g) in EtOH (50 ml) is heated to reflux for two hours, then cooled to room temperature, acidified with a few drops of AcOH and diluted with iced water (500 ml). The precipitate is filtered off, dried in vacuum and recrystallized from $Et_2O$ to give 3.2 g of 2-mercaptomethyl-3,5-dicarboethoxy-4-(m-nitrophenyl)-6-methyl-1,4-dihydropyridine, m.p. 145°–147° C.

EXAMPLE 5

Using in the procedures described in the Examples 1–4 a suitable 2-halomethyl-1,4-dihydropyridine of formula II, the following 2-mercaptomethyl-6-methyl-1,4-dihydropyridine are prepared:
3-carboethoxy-5-carbomethoxy-4-(m-nitrophenyl); m.p. 104°–107° C.;
3-carboethoxy-5-carbomethoxy-4-(m-chlorophenyl); m.p. 85°–90° C.;
3,5-dicarboethoxy-4-(m-trifluoromethylphenyl)); m.p. 102°–103° C.;
3-carboethoxy-5-carboisopropoxy-4-(o-methylthiophenyl);
3,5-dicarbomethoxy-4-(o-difluoromethoxyphenyl);
3,5-dicarbomethoxy-4-(β-pyridyl);
3,5-dicarboethoxy-4-phenyl;
3,5-dicarboethoxy-4-(p-fluorophenyl);
3,5-dicarboethoxy-(2-furanyl);
3-carboethoxy-5-nitro-4-(m-nitrophenyl);
3-carboethoxy-5-cyano-4-(o-trifluoromethylphenyl).

EXAMPLE 6

Using a suitable 2-halomethyl-1,4-dihydropyridine of formula II in the procedure of the Example 3, the following 2-acetylthiomethyl-3,5-substituted-4-(substituted phenyl)-6-methyl-1,4-dihydropyridine are prepared:
3,5-dicarboethoxy-4-(m-nitrophenyl); m.p. 113°–115° C.;
3-carboethoxy-5-carbomethoxy-4-(m-nitrophenyl); m.p. 80°–82° C.;
3,5-dicarboethoxy-4-(m-trifluoromethylphenyl);
3-carboethoxy-5-nitro-4-(m-nitrophenyl);
3,5-dicarbomethoxy-(α-thienyl); - 3-carboethoxy-5-carbomethoxy-4-(o-chlorophenyl); m.p. 141°–145° C.;
3,5-dicarboethoxy-4-(o-chlorophenyl); m.p. 104°–105° C.

EXAMPLE 7

Using in the procedure of Example 4 a thiono-imide (—CS—NH—) compound selected from the group consisting of thiourea, 1-methyl-2-thiourea, 1,3-dimethyl-2-thiourea, 2-imidazolidinethione and 3,4,5,6-tetrahydro-2-thio-pyrimidine and a suitable 2-chloromethyl-1,4-dihydropyridine the following compounds are prepared:
S-[(6-methyl-3,5-dicarbomethoxy-4-(m-chlorophenyl)-1,4- dihydropyridin-2-yl)methyl]isothiouronium hydrochloride;
S-[(6-methyl-3-carboethoxy-5-cyano-4-(o-trifluoromethyl-phenyl)-1,4-diydropyridin-2-yl)methyl-]isothiouronium fumarate;
S-[(6-methyl-3,5-dicarboethoxy-4-phenyl-1,4-dihydropyridin-2-yl)methyl]1-methylisothiouronium hydrochloride;
S-[(6-methyl-3,5-dicarboethoxy-4-(p-fluorophenyl)-1,4-dihydropyridin-2-yl)methyl]-1,3-dimethylisothiouronium hydrochloride;
2-[(1,4,5,6-tetrahydropyrimid-2-yl)thio]methyl-3,5-dicarboethoxy-6-methyl-4-(m-nitrophenyl)-6-methyl-1,4-dihydropyridine hydrochloride, m.p. 217°–219° C.;
2-[4,5-dihydroimidazol-2-yl)thio]methyl-3-carbomethoxy-5-carboethoxy-4-(m-trifluoromethylphenyl)-6- methyl-1,4-dihydropyridine hydrochloride; m.p. 190°-192° C.;

2-[4,5-dihydroimidazol-2-yl)thio]methyl-3,5-dicarboethoxy-4-(m-nitrophenyl)-6-methyl-1,4-dihydropyridine hydrochloride, m.p. 211°-213°.

EXAMPLE 8

A mixture of 2-mercaptomethyl-3,5-dicarboethoxy-4-(m-nitrophenyl)-6-metyl-1,4-dihydropyridine (4.05 g), propionyl chloride (0.88 ml), and TEA (1.4 ml) in methylene chloride (50 ml) is stirred at room temperature, under $N_2$ atmosphere for two hours.

The reaction mixture is evaporated to dryness in vacuum, the residue partitioned between AcOEt (50 ml) and water (2×30 ml); the organic layer, dried on $Na_2SO_4$ is evaporated in vacuum. The residue is purified by $SiO_2$ column chromatography (eluent: hexane/AcOEt 7/3) to give 3.6 g of 2-(propionylthio)methyl-3,5-dicarboethoxy-4-(m-nitrophenyl)-6-methyl-1,4-dihydropyridine oil.

NMR $(CDCl_3)\delta$(TMS): 1.10–1.40 (9H, m); 2.20 (3H, s); 2.50 (2H, q); 3.80–4.20 (6H, m); 5.10 (1H, m); 6.90–8.10 (5H, m).

EXAMPLE 9

Using in the procedure of Example 8 an acylchloride selected in the group of propionyl chloride, hexanoyl chloride, heptanoyl and decanoyl chloride and a suitable 2-mercaptomethyl-6-methyl-1,4-dihydropyridine, the following 6-methyl-1,4-dihydropyridine are obtained:

2-(propionylthio)methyl-3,5-dicarboethoxy-4-(o-chlorophenyl); oil 2-(heptanoylthio)methyl-3-carboethoxy-5-carboisopropoxy-4-(m-nitrophenyl); oil 2-(hexanoylthio)methyl-3-carboethoxy-5-carbomethoxy-4-(m-chlorophenyl); oil 2-(decanoylthiomethyl)-3,5-dicarbomethoxy-4-(p-nitrophenyl); oil.

EXAMPLE 10

A solution of 2-chloromethyl-3,5-dicarboethoxy-4-(m-nitrophenyl)-6-methyl-1,4-dihydropyridine (5.6 g) in EtOH/DME (5/1; 20 ml) is added dropwise at +10° C. to a stirred solution of sodium thiophenate (1.8 g) in ethanol (10 ml), under $N_2$ atmosphere. After two hours at room temperature the reaction mixture is evaporated under vacuum and the residue is partitioned between $Et_2O$ (100 ml) and water (50 ml). The organic phase is washed with a satured solution of sodium bicarbonate (2×20 ml) and water (3×20 ml), dried ($Na_2SO_4$) and evaporated to dryness. The residue is recrystallized from isopropylether to give 5.7 g of 2-(phenylthio)methyl-3,5-dicarboethoxy-4-(m-nitrophenyl)-6-methyl-1,4-dihydropyridine, m.p. 92°-94° C.

EXAMPLE 11

Using in the procedure of Example 10 a substituted thiophenol and a suitable 2-chloromethyl-1,4-dihydropyridine the compounds listed in the following Table are prepared.

TABLE

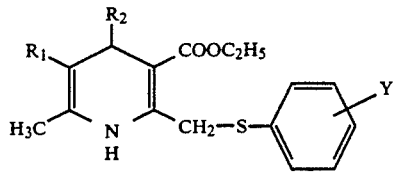

| $R_1$ | $R_2$ | Y | M.p. (°C.) |
|---|---|---|---|
| $CO_2Et$ | $o$-$NO_2$—$C_6H_5$ | H | 135–136 |
| $CO_2Me$ | $m$-$NO_2$—$C_6H_5$ | H | 125–126 |
| $CO_2Et$ | $m$-Cl—$C_6H_5$ | H | oil |
| $CO_2Et$ | $m$-$CF_3$—$C_6H_5$ | H | oil |
| $CO_2Et$ | $o$-Cl—$C_6H_5$ | H | oil |
| CN | $m$-$NO_2$—$C_6H_5$ | H | oil |
| $NO_2$ | $m$-$NO_2$—$C_6H_5$ | H | oil |
| $CO_2Me$ | $\beta$-pyridyl | H | oil |
| $CO_2Me$ | $\alpha$-furanyl | H | oil |
| $CO_2Et$ | $m$-$NO_2$—$C_6H_5$ | $o$-COOH | 179–181 |
| $CO_2Et$ | $m$-$NO_2$—$C_6H_5$ | $p$-$OCH_3$ | 164–166 |
| $CO_2Et$ | $m$-$NO_2$—$C_6H_5$ | $p$-F | 103–105 |
| $CO_3Et$ | $m$-$NO_2$—$C_6H_5$ | $p$-Cl | 124–126 |
| $CO_2Et$ | $m$-$NO_2$—$C_6H_5$ | $p$-$NHCOCH_3$ | 166–168 |
| $CO_2Et$ | $m$-$NO_2$—$C_6H_5$ | $p$-$NH_2$ | 104–106 |
| CN | $m$-$NO_2$—$C_6H_5$ | $p$-$NHCOCH_3$ | 60–63 |
| $CO_2Et$ | $\beta$-pyridyl | $p$-F | oil |
| $CO_2Et$ | $m$-$NO_2$—$C_6H_5$ | $o$-$NH_2$ | 104–106 |

EXAMPLE 12

A mixture of 2-mercaptomethyl-3,5-dicarboethoxy-4-(m-nitrophenyl)-6-methyl-1,4-dihydropyridine (4.8 g), 2-bromoethylbenzene (2.3 g), tetrabutylammonium bromide (0.150 g), toluene (50 ml) and sodium hydroxide (1N water solution, 12 ml) is stirred at room temperature, under $N_2$ atmosphere, for two hours.

The organic phase is separated, washed with a satured aqueous solution of $NaH_2PO_4$(2×20 ml) and water (3×20 ml), dried on $Na_2SO_4$ and evaporated to dryness in vacuum. The residue is purified by $SiO_2$ column chromatography (150 g, hexane/AcOEt 80/20, as eluent), to give 4.4 g of 2-[(2-phenylethyl)thio]methyl-3,5-dicarboethoxy-4-(m-nitrophenyl)-6-methyl-1,4-dihydropyridine, m.p. 73°-75° C.

EXAMPLE 13

Using the procedure of Example 12 the following compounds are prepared:

2-[(phenylmethyl)thio]methyl-3,5-dicarboethoxy-4-(m-nitrophenyl)-6-methyl-1,4-dihydropyridine; m.p. 91°-93° C.;

2-[(phenylmethyl)thio]methyl-3,5-dicarboethoxy-4-(o-chlorophenyl)-6-methyl-1,4-dihydropyridine; oil;

2-[(phenylethyl)thio]methyl-3-carboethoxy-5-carbomethoxy-4-(o-methylthiophenyl)-6-methyl-1,4-dihydropropyridine; oil.

EXAMPLE 14

A solution of 2-chloromethyl-3,5-dicarboethoxy-4-(m-nitrophenyl)-6-methyl-1,4-dihydropyridine (2.5 g) in EtOH (25 ml) is added dropwise at −10° C. to a solution of 2-mercaptopyrimidine (0.77 g) and sodium hydroxide (35% water solution, 0.84 ml) in EtOH (15 ml).

After two hours the solution is acidified with a few drops of AcOH and evaporated under reduced pressure; the residue is dissolved in AcOEt (50 ml), the organic phase is washed with water (4×10 ml), dried on $Na_2SO_4$ and evaporated to dryness. The residue is crystallized from EtOH to give 2-[(2-pyrimidyl)thio-]methyl-3,5-dicarboethoxy-4-(m-nitrophenyl)-6-methyl-1,4-dihydropyridine (2.7 g, m.p. 115°–117° C.).

EXAMPLE 15

Using in the procedure of Example 14 a suitable heterocyclic thiol of formula III, the compounds listed in the following Tables are prepared:

TABLE

| R | m.p. (°C.) |
|---|---|
| furan-2-yl-CH₂S— | 73–75 |
| thiazoline-2-yl-S— | 118–120 |
| 1-methylimidazol-2-yl-S— | 131–133 |
| 1-methyl-1,2,4-triazole-3-thione-5-yl | 133–135 |
| 1H-1,2,4-triazol-3-yl-S— | 113–115 |
| 1-methyltetrazol-5-yl-S | 102–105 |
| 4-(ethoxycarbonyl)-5-(phenoxymethyl)thiazol-2-yl-S— | oil |
| 5-amino-1,2,4-triazol-3-yl-S— | 104–107 |
| 5-amino-1,3,4-thiadiazol-2-yl-S— | 116–120 |

TABLE-continued

| R | m.p. (°C.) |
|---|---|
| 5-amino-1H-1,2,4-triazol-3-yl-S— | 104–107 |
| benzoxazol-2-yl-S— | 99–101 |
| benzimidazol-2-yl-S— | 161–163 |
| pyridin-4-yl-S— | 177–179 |
| pyridin-2-yl-N-oxide-S— | 72–74 |
| 3-hydroxypyridin-2-yl-S— | 148–150 |
| pyridin-2-yl-CH₂S— | oil |
| pyridin-2-yl-CH₂CH₂S— | oil |
| 2-benzamido-phenyl-N=C-S— | 200–202 |

TABLE

Structure: 1,4-dihydropyridine with R₁ at 5-position, R₂ at 4-position, COOEt at 3-position, H₃C at 6-position, NH, and CH₂-S-pyrimidinyl at 2-position.

| R₁ | R₂ | m.p. (°C) |
|---|---|---|
| CO₂Et | o-Cl—C₆H₅ | oil |
| CO₂Me | m-CF₃—C₆H₅ | oil |
| CO₂Me | β-pyridyl | oil |
| CN | m-NO₂—C₆H₅ | 163–165 |
| NO₂ | o-CF₃ | oil |

EXAMPLE 16

A solution of monoperphtalic acid in AcOEt (0.37 M solution; 20 ml) is added at 0° C. to a mixture of 2-(phenylthio) methyl-3,5-dicarboethoxy-4-(m-nitrophenyl)-6-methyl-1,4-dihydropyridine (3.5 g) and NaHCO₃ (3 g) in AcOEt (20 ml). After 30 minutes the mixture is filtered and the eluate is washed with 1N solution of sodium thiosulfate (2×20 ml) and then with water (3×10 ml). The organic layer is dried on Na₂SO₄ and evaporated to dryness; the residue is purified by chromatography on SiO₂ (hexane/AcOEt 85/15, as eluent) to give 3.5 g of 2-(phenylsulfinyl)methyl-3,5-dicarboethoxy-4-(m-nitrophenyl)-6-methyl-1,4-dihydropyridine, m.p. 160°–162° C.

EXAMPLE 17

Using the procedure of Example 16 the following compounds are prepared:

TABLE

Structure: 4-(X-phenyl)-3,5-di(ethoxycarbonyl)-6-methyl-2-(CH₂-R)-1,4-dihydropyridine.

| X | R | M.p. (°C) |
|---|---|---|
| mNO₂ | 4-CH₃O—C₆H₄—S(O)— | 158–162 |
| mNO₂ | 4-F—C₆H₄—S(O)— | 168–170 |
| mNO₂ | 4-Cl—C₆H₄—S(O)— | 169–171 |
| mNO₂ | C₆H₅—S(O)— | 157–161 |
| oNO₂ | C₆H₅—S(O)— | oil |
| oCl | C₆H₅—S(O)— | oil |
| mNO₂ | φCH₂O—C(=)—C(EtOOC)=... N-heterocycle—S(O)— | oil |
| mNO₂ | N-methylimidazolyl—S(O)— | 157–159 |
| mNO₂ | 4-pyridyl—S(O)— | oil |

EXAMPLE 18

A solution of 1-chloro-2-pentanone (1.6 g) in THF (15 ml) is added, at 0° C., under N₂ atmosphere, to a solution of the sodium salt of 2-mercaptomethyl-3-carboethoxy-5-carbomethoxy-4-(m-nitrophenyl)-6-methyl-1,4-dihydropyridine (5.2 g), (prepared in situ from the corresponding thiol and NaH) in THF (30 ml).

The reaction mixture is stirred at room temperature for two hours, then AcOEt is added (150 ml), the organic phase is washed with a saturated aqueous solution of NaH₂PO₄ (2×20 ml), dried on Na₂SO₄ and evaporated to dryness. The residue is recrystallized from Et₂O to give 4.25 g of 2-[(2-oxopentyl)thio]methyl-3-carboethoxy-5-carbomethoxy-4-m-(nitrophenyl)-6-methyl-1,4-dihydropyridine, m.p. 128°–130° C.

EXAMPLE 19

Reacting a suitable 2-mercaptomethyl-1,4-dihydropyridine, prepared according to the procedures of the Example 1–4 with an activated halo compound selected from the group consisting of bromoacetone, ethyl-4-chloroacetoacetate, ethyl-3-bromopyruvate, phenacyl bromide, 1-bromo-3-phenyl-2-propanone, 1-bromo-5-acetylamino-2-pentanone, 1-bromo-6-acetylamino-2-hexanone, 1-bromo-2,2-diethoxyethane, 1-bromo-2,2-dimethoxyethane, ethylchloroacetate, epichloridrine, epibromidrine, N-(4-bromobutyl)phtalimide and p-(imidazol-1-yl)-1-bromoacetophenone and carrying out the reaction as described in one of the Examples 12 and 18, the following compounds are prepared:

2-[(2-oxopropyl)thio]methyl-3-carboethoxy-5-carbomethoxy-4-(m-nitrophenyl)-6-methyl-1,4-dihydropyridine; oil;

2-[(3-carboethoxy-2-oxopropyl)thio]methyl-3-carboethoxy-5-carbomethoxy-4-(m-nitrophenyl)-6-methyl-1,4-dihydro pyridine; oil;

2-[(2-phenyl-2-oxo-ethyl)thio]methyl-3-carboethoxy-5-carbomethoxy-4-(m-nitrophenyl)-6-methyl-1,4-dihydropyridine; m.p. 152°–154° C.;

2-[(3-phenyl-2-oxo-propyl)thio]methyl-3-carboethoxy-5-carbomethoxy-4-(m-nitrophenyl)-6-methyl-1,4-dihydropyridine; oil;

2-[(3-phenyl-2-oxo-propyl)thio]methyl-3-carboethoxy-5-carbomethoxy-4-(m-trifluoromethylphenyl)-6-methyl-1,4-dihydropyridine; oil;

2-[(5-acetylamino-2-oxo-pentyl)]methyl-3-carboethoxy-5-carbomethoxy-4-(m-nitrophenyl)-6-methyl-1,4-dihydropyridine; oil;

2-[(6-acetylamino-2-oxo-hexyl)thio]methyl-3-carboethoxy-5-carbomethoxy-4-(m-nitrophenyl)-6-methyl-1,4-dihydropyridine; oil;

2-[2,2-diethoxyethyl)thio]methyl-3-carboethoxy-5-carbomethoxy-4-(m-nitrophenyl)-6-methyl-1,4-dihydropyridine; amorphous solid;

2-[(2,2-dimethoxyethyl)thio]methyl-3-carboethoxy-5-carbomethoxy-4-(m-trifluoromethylphenyl)-6-methyl-1,4-dihydropyridine; amorphous solid;

2-[(oxiran-2-yl)methylthio]methyl-3,5-dicarboethoxy-4-(m-nitrophenyl)-6-methyl-1,4-dihydropyridine m.p. 107°–109° C.;

2-[(oxiran-2-yl)methylthio]methyl-3-carboethoxy-5-carbomethoxy-4-(m-nitrophenyl)-6-methyl-1,4-dihydropyridine, m.p. 100°–103° C.;

2-[(oxiran-2-yl)methylthio]methyl-3-carboethoxy-5-carbomethoxy-4-(m-chlorophenyl)-6-methyl-1,4-dihydropyridine, m.p. 80°–84° C.;

2-[4-((N-phtalimido)butylthio]methyl-3-carboethoxy-5-carbomethoxy-4-(m-nitrophenyl)-6-methyl-1,4-dihydropyridine, m.p. 125°–127° C.;

2-(carboethoxymethylthio)methyl-3,5-dicarboethoxy-4-(m-nitrophenyl)-1,4-dihydropyridine; oil;

2-[2-(4-imidazol-1-yl)phenyl-2-oxoethylthio]methyl-3,5-dicarboethoxy-4-(m-trifluoromethylphenyl)-6-methyl-1,4-dihydropyridine.

EXAMPLE 20

A solution of 2-(pyrrolidin-1-yl)-1-chloroethane hydrochloride (2.8 g), 2-mercaptomethyl-3,5-dicarboethoxy-4-(m-nitrophenyl)-6-methyl-1,4-dihydropyridine (5.4 g) and sodium ethoxide (2 g) in ethanol (70 ml) is heated to the reflux temperature for 6 hours, then it is neutralized with AcOH and evaporated under reduced pressure. The residue, after the usual work-up, is purified by column-chromatography (SiO2; 210 g; eluent AcOH/MeOH 99/1) to give 2.8 g of 2-[2-(pyrrolidin-1-yl)ethylthio]methyl-3,5-dicarboethoxy-4-(m-nitrophenyl)-6-methyl-1,4-dihydropyridine, as an oil, that upon treatment with fumaric acid gives the corresponding salt, m.p. 192°–194° C.

EXAMPLE 21

Using in the procedure of the Example 20, instead of 2-(pyrrolidin-1-yl)-1-chloroethane a chloro compound selected from 2-(piperidin-1-yl)-1-chloroethane, 2-(morpholin-4-yl)-1-chloroethane and 2-(4-methylpiperazin-1-yl)-1-chloroethane the following 3-carboethoxy-5-carbomethoxy-4-(m-nitrophenyl)-6-methyl-1,4-dihydropyridines are obtained:

2-[2-(morpholin-4-yl)ethylthio]methyl hydrochloride; m.p. 204°–208° C.;

2-[2-(piperidin-1-yl)ethylthio]methyl;

2-[2-(4-methylpiperazin-1-yl)ethylthio]methyl.

EXAMPLE 22

A THF solution (25 ml) of 2-[(2,2-diethoxyethyl)-thio]methyl-3-carboethoxy-5-carbomethoxy-4-(m-nitrophenyl)-6-methyl-1,4-dihydropyridine (5 g), hydroquinone (0.5 g), and oxalic acid (1N water solution, 10 ml) is heated to the reflux temperature, under N2 atmosphere, for one hour, then the THF is evaporated in vacuum and the water layer is extracted with AcOEt (3×20 ml). The organic phases are washed with water (2×5 ml), a satured solution of NaHCO3 (2×5 ml) and water (3×5 ml), dried on Na2SO4 and evaporated to dryness. The residue, after purification by column chromatography (SiO2 120 g; eluent: hexane/isopropyl ether 70/30), yields 3.8 g of pure 2-[(formylmethyl)thio]methyl-3-carboethoxy-5-carbomethoxy-4-(m-nitrophenyl)-6-methyl-1,4-dihydropyridine, oil.

NMR (CDCl3)δ(TMS): 1.10–1.40 (3H, t); 2.40 (3H, s); 3.35 (2H, d); 3.70 (3H, s); 3.80–4.30 (4H, m); 5.10 (1H, s); 7.20–8.20 (5H, m); 9.50 (1H, m).

Using the same procedure described above the following compound is prepared: 2-[(formylmethyl)thio]methyl-3-carboethoxy-5-carbomethoxy-4-(m-trifluoromethylphenyl)-6-methyl-1,4-dihydropyridine (oil).

EXAMPLE 23

A solution of 2-chloromethyl-3-carboethoxy-5-carbomethoxy-4-(m-nitrophenyl)-6-methyl-1,4-dihydropyridine (10 g) in EtOH/DME (5/1; 25 ml) is added dropwise under nitrogen at −10° C. to a solution of cysteamine hydrochloride (3.1 g) and sodium hydroxide (20% water solution, 8.6 ml) in EtOH (60 ml). After 30 minutes the reaction is warmed to room temperature, acidified (pH ≃ 4.5) with AcOH and evaporated under vacuum. The residue is dissolved in water and washed with Et2O (3×30 ml). The ethereal extracts are discarded and the water layer is made basic with a Na2CO3 solution and extracted with AcOEt/Et2O (1/1; 5×50 ml). The organic layers are dried on Na2SO4 and evaporated to dryness to give 10.5 g of 2-[(2-aminoethyl)thio]methyl-3-carboethoxy-5-carbomethoxy-4-(m-nitrophenyl)-6-methyl-1,4-dihydropyridine $C_{20}H_{25}N_3O_6S$.

Said compound (10.5 g) is dissolved in AcOEt (180 ml) at 40° C. and a solution of fumaric acid (2.8 g) in methanol (30 ml), heated at 60° C., is added to give, after cooling, 12 g of the corresponding fumarate $C_{20}H_{25}N_3O_6S \cdot C_4H_4O_4$, m.p. 170°–172° C.

EXAMPLE 24

Using in the procedure of Example 23 cysteamine hydrochloride and a 2-chloromethyl-3,5-dicarboxyesters-4-substituted-6-methyl-1,4-dihydropyridine the compounds listed in the following tables are prepared.

TABLE

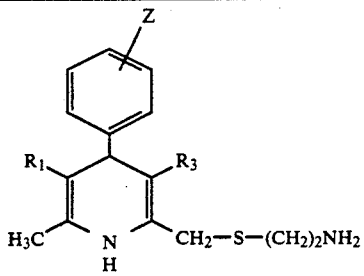

| $R_1$ | Z | $R_3$ | m.p. (°C.) | (Form characterized) |
|---|---|---|---|---|
| $CO_2Et$ | m-$NO_2$ | $CO_2Et$ | 95–97 | (base) |
| $CO_2Me$ | m-$NO_2$ | $CO_2Me$ | 145–148 | (hydrochloride) |
| $CO_2C_3H_7$-i | m-$NO_2$ | $CO_2Et$ | 95–98 | (hydrochloride) |
| $CO_2Et$ | o-Cl | $CO_2Et$ | 106–109 | (base) |
| $CO_2Me$ | o-Cl | $CO_2Et$ | 124–125 | (base) |
| $CO_2Me$ | m-Cl | $CO_2Et$ | 148–152 | (fumarate) |
| $CO_2Et$ | o-$CF_3$ | $CO_2Et$ | 85–88 | (base) |
| $CO_2Me$ | m-$CF_3$ | $CO_2Et$ | 112–115 | (hydrochloride) |
| $CO_2Me$ | o-$CF_3$ | $CO_2Et$ | 103–105 | (base) |
| $CO_2Me$ | H | $CO_2Et$ | 99–100.5 | (base) |
| $CO_2Me$ | p-$NO_2$ | $CO_2Et$ | 140–142 | (fumarate) |
| COOEt | 2,3-dichloro | COOEt | oil | (base) |
| COOEt | o-$CHF_2O$— | COOEt | oil | (base) |
| $COOC_3H_7$-i | o-$NO_2$ | COOMe | oil | (base) |

TABLE

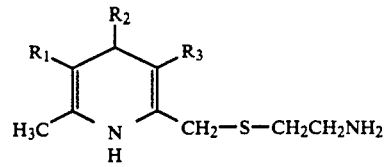

| $R_1$ | $R_2$ | $R_3$ | m.p. (°C.) |
|---|---|---|---|
| $CO_2Me$ | β-pyridyl | $CO_2Me$ | oil (base) |
| $CO_2Et$ | α-thienyl | $CO_2CH(CH_3)_2$ | oil (base) |
| $CO_2CH(CH_3)_2$ | α-furanyl | $CO_2Me$ | oil (base) |

EXAMPLE 25

Using in the procedure of Example 24 a 2-chloromethyl-3,5-dicarboxyesters-4-(substituted phenyl)-6-methyl-1,4-dihydropyridine and a thiol selected from the group of N,N-dimethylcysteamine, N-methylcysteamine, N-butylcysteamine, 3-(N-phtalimido)-propylmercaptane, N-acetylcysteamine, 2-mercaptoethanol, 3-mercapto-1,2-propanediol, L-cysteine, L-cysteine ethyl ester, glutathione, D-cysteine methyl ester and glutathione diethyl esters the compounds listed in the following Table are prepared.

TABLE

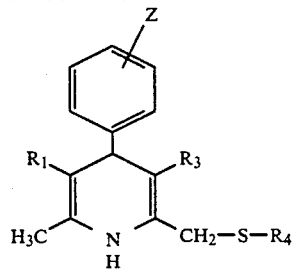

| $R_1$ | Z | $R_3$ | $R_4$ | m.p. (°C.) | (form characterized) |
|---|---|---|---|---|---|
| $CO_2Me$ | m-$NO_2$ | $CO_2Et$ | $CH_2CH_2N(CH_3)_2$ | 191–194 | (hydrochloride) |
| $CO_2Me$ | m-$NO_2$ | $CO_2Et$ | $CH_2CH_2NHCH_3$ | 205–207 | (fumarate) |
| $CO_2Me$ | m-$NO_2$ | $CO_2Et$ | $CH_2CH_2NH$—$C_4H_9$-n | 105–107 | (base) |
| $CO_2Et$ | m-$NO_2$ | $CO_2Et$ | $CH_2CH_2NHC_4H_9$-n | 129–131 | (hydrochloride) |
| $CO_2Me$ | m-$NO_2$ | $CO_2Et$ | $CH_2CH_2NPhth^{(1)}$ | 140–142 | — |
| $CO_2Me$ | m-$NO_2$ | $CO_2Et$ | $CH_2CH_2NHCOCH_3$ | 115–116 | — |
| $CO_2Et$ | m-$NO_2$ | $CO_2Et$ | $CH_2CH_2NHCOCH_3$ | 68–71 | — |
| $CO_2Et$ | o-Cl | $CO_2Et$ | $CH_2CH_2NHCHCO_3$ | oil | — |
| $CO_2Me$ | o-$CF_3$ | $CO_2Me$ | $CH_2CH_2NHCOCH_3$ | oil | — |
| $CO_3Et$ | m-$NO_2$ | $CO_2Et$ | $CH_2$—$CH(OH)CH_2OH$ | 98–102 | — |
| $CO_2Me$ | o-Cl | $CO_2Et$ | $CH_2CH(OH)$—$CH_2OH$ | oil | — |
| $CO_2Et$ | m-$NO_2$ | $CO_2Et$ | $CH_2CH_2OH$ | 119–120 | — |
| $CO_2Et$ | m-$NO_2$ | $CO_2Et$ | $CH_2$—$CH(NH_2)CO_2Et$ | 130–135 | (hydrochloride) |
| $CO_2Me$ | m-$NO_2$ | $CO_2Et$ | $CH_2CH(NH_2)CO_2Et$ | amorphous solid | (base) |
| $CO_2Et$ | m-$NO_2$ | $CO_2Et$ | $CH_2CH(NH_2)COOH$ | 128–131 | (base) |
| $CO_2Et$ | m-$NO_2$ | $CO_2Et$ | G—$^{(2)}$ | oil | — |
| $CO_2Et$ | m-$NO_2$ | $CO_2Et$ | G-diethylester$^{(3)}$ | oil | — |
| COOEt | m-$CF_3$ | COOEt | $CH_2CH(NH_2)COOMe$ | oil | — |

$^{(1)}$Phth: phtaloyl $^{(2)}$G: glutathionyl = $HO_2C$—$CH(NH_2)$—$CH_2CH_2CONHCH$—$CONHCH_2CO_2H$
                                                                    |
                                                                   —$CH_2$ $^{(3)}$G-diethylester = $EtO_2C$—$CH(NH_2)CH_2CH_2CONH$—$CH$—$CONHCH_2CO_2Et$
                                                          |
                                                         —$CH_2$

EXAMPLE 26

A solution of 2-chloromethyl-3-carboethoxy-4-(m-nitrophenyl)-5-nitro-6-methyl-1,4-dihydropyridine (1.5 g) in EtOH (15 ml) is added dropwise at 0° C. under $N_2$ atmosphere to a solution of cysteamine hydrochloride (0.9 g) and sodium hydroxide (0.32 g) in EtOH (45 ml). After two hours the solution is acidified (pH ≃ 4) with AcOH, evaporated under reduced pressure and the residue is dissolved in water (50 ml) and extracted with Et$_2$O (2×20 ml). The ethereal extractions are discarded, the water layer is made basic with NaHCO$_3$ and extracted with AcOEt (2×20 ml); the organic phase is washed with water (3×10 ml), dried (Na$_2$SO$_4$), added to a solution of fumaric acid (0.45 g) in MeOH (15 ml), and evaporated to dryness. The residue is crystallized from AcOEt to give 1.9 g of 2-[(2-aminoethyl)thio]-methyl-3-carboethoxy-4-(m-nitrophenyl)-5-nitro-6-methyl-1,4-dihydropyridine fumarate (C$_{18}$H$_{22}$N$_4$O$_6$S.C$_4$H$_4$O$_4$), m.p. 182°–185° C.

According to the above procedure, the following compounds are prepared:

2-[(2-(N-n-butylaminoethyl)thio]methyl-3-carboethoxy-4-(m-nitrophenyl)-5-nitro-6-methyl-1,4-dihydropyridine fumarate; m.p. 198°–200° C.;

2-[(2-aminoethyl)thio]methyl-3-carboethoxy-4-(m-trifluoromethylphenyl)-5-nitro-6-methyl-1,4-dihydropyridine fumarate; m.p. 152°–155° C.;

2-[(2-aminoethyl)thio]methyl-3-carboethoxy-4-(m-nitrophenyl)-5-cyano-6-methyl-1,4-dihydropyridine fumarate; m.p. 181°–183° C.;

2-[(2-(N-n-butylaminoethyl)thio]methyl-3-carboethoxy-4-m-nitrophenyl)-5-cyano-6-methyl-1,4-dihydropyridine fumarate; m.p. 172°–175° C.;

2-[(2-aminoethyl)thio]methyl-3-carboethoxy-4-(m-nitrophenyl)-5-acetyl-6-methyl-1,4-dihydropyridine, oil;

2-[(2-aminoethyl)thio]methyl-3-carboethoxy-4-(m-nitrophenyl)-5-benzoyl-6-methyl-1,4-dihydropyridine, oil.

EXAMPLE 27

A solution of 2-[(2,3-dihydroxypropyl)thio]methyl-3,5-dicarboethoxy-4-(m-nitrophenyl)-6-methyl-1,4-dihydropyridine (5 g) and tosyl chloride (2 g) in pyridine (25 ml) is stirred at 0° C. for two hours, then it is poured into iced water (250 ml) and extracted with Et$_2$O (100 ml). The ethereal solution is washed with aqueous 2N H$_2$SO$_4$ (2×20 ml), and with water (2×30 ml), dried (Na$_2$SO$_4$) and evaporated to dryness.

The residue (6 g) is dissolved at room temperature in THF (60 ml) and sodium hydroxide (4N water solution, 2.5 ml); after four hours the solution is neutralized with AcOH and evaporated in vacuum. After the usual work-up the residue is purified by column chromatography (SiO$_2$, 240 g, eluent: hexane/AcOEt 70/30) to give 3.2 g of 2-[(oxiran-2-yl)methylthio]methyl-3,5-dicarboethoxy-4-(m-nitrophenyl)6-methyl-1,4-dihydropyridine, m.p. 107°–109° C.

EXAMPLE 28

A solution of 2-[(oxiran-2-yl)methylthio]methyl-3,5-dicarboethoxy-4-(m-nitrophenyl)-6-methyl-1,4-dihydropyridine (2.5 g) and isopropylamine (5.5 ml) in DME (20 ml) is heated to reflux for two hours, then it is evaporated to dryness and the residue purified by column chromatography (SiO$_2$ 75 g; eluent: CHCl$_3$/MeOH 95/5) to give 2.3 g of pure 2-[(3-N-isopropylamino-2-hydroxypropyl)thio-methyl-3,5-dicarboethoxy-4-(m-nitrophenyl)-6-methyl-1,4-dihydropyridine amorphous solid.

NMR (CDCl$_3$) δ (TMS): 0.8–1.30 (12H, m); 2.25 (3H, s); 2.45–3.00 (4H, m); 3.20–3.80 (4H, m); 3.80–4.30 (6H, m); 5.10 (1H, s); 6.90–8.30 (5H, m).

EXAMPLE 29

Using in the procedure described in Example 28 ammonia and 1-[bis-(p-fluorophenyl)]methyl-piperazine and a suitable 2-[(oxiran-2-yl)methylthio]methyl-1,4-dihydropyridine the following compounds are obtained:

2-[(3-amino-2-hydroxypropyl)]methyl-3-carboethoxy-5-carbomethoxy-4-(m-nitrophenyl)-6-methyl-1,4dihydropyridine, oil;

2-[3-(4-bis-p-fluorophenylmethyl-piperazin-1-yl)-2-hydroxypropylthio]methyl-3-carboethoxy-5-carbomethoxy-4-(m-nitrophenyl)-6-methyl-1,4-dihydropyridine, oil.

EXAMPLE 30

A mixture of 2-[(2-carboethoxy-2-aminoethyl)thio]methyl-3-carboethoxy-5-carbomethoxy-4-(m-nitrophenyl)-6-methyl-1,4-dihydropyridine hydrochloride (3.7 g) and sodium borohydride (1.3 g) in EtOH 95% (50 ml) is stirred under N$_2$ atmosphere for 18 hours, then it is acidified (pH -4) with AcOH and evaporated in vacuum. The residue is dissolved in water (50 ml) and washed with Et$_2$O (3×20 ml). The organic phase is discarded, the aqueous phase is made basic with a few drops of NaOH (1N solution) and extracted with AcOEt (3×20 ml). The organic layers are then dried (Na$_2$SO$_4$), evaporated to dryness and the residue purified by column chromatography (SiO$_2$, 120 g; eluent: AcOEt/MeOH 80/20) to give 2.8 g of pure 2-[(3-hydroxy-2-amino-propylthio]methyl-3-carboethoxy-5-carbomethoxy-4-(m-nitrophenyl)-6-methyl-1,4-dihydropyridine as an oil. After salification, 2.8 g of the corresponding fumarate, m.p. 68°–71° C. are obtained.

EXAMPLE 31

A solution of 2-mercaptomethyl-3,5-dicarboethoxy-4-(m-nitrophenyl)-6-methyl-1,4-dihydropyridine (5 g), acrylonitrile (0.66 g) and 1,1,3,3-tetramethylguanidine (0.1 g) in EtOH (60 ml) is stirred at room temperature for 18 hours and then evaporated to dryness. After the usual work-up, the residue is recrystallized from Et$_2$O to give 5.2 g of 2-[(2-cyanoethyl)thio]methyl-3,5-dicarboethoxy-4-(m-nitrophenyl)-6-methyl-1,4-dihydropyridine m.p. 102°–104° C.

EXAMPLE 32

Using in the procedure of Example 31 an α-β-unsatured-oxo compound selected from: cinnamaldehyde, ethyl acrylate, acrylamide, 1-phenyl-1-oxo-2-propene, 1-(p-imidazol-1-yl)phenyl-1-oxo-2-propene, 2-cyclohexen-1-one and 2-mercaptomethyl-3,5-dicarboethoxy-4-(m-nitrophenyl)-6-methyl-1,4-dihydropyridine, the following 3,5-dicarboethoxy-4-(m-nitrophenyl)-6-methyl-1,4-dihydropyridine are prepared:

2-[(3-oxo-1-phenylpropyl)thio]methyl;
2-[(2-carboethoxyethyl)thio]methyl;
2-[(3-oxo-3-phenylpropyl)thio]methyl;
2-[(3-oxo-3-(p-imidazolyl)phenylpropyl)thio]methyl;
2-[(3-oxo-cyclohexen-1-yl)thio]methyl;
2-[(2-carbamoylethyl)thio]methyl.

EXAMPLE 33

A mixture of 2-[(2-oxopropyl)thio]methyl-3-carboethoxy-5-carbomethoxy-4-(m-nitrophenyl)-6-methyl-1,4-dihydropyridine (3 g), ammonium acetate (6 g) and sodium cyanoborohydride (0.43 g) in MeOH/1,2-dichloroethane (3/1; 20 ml) is stirred under N$_2$ atmosphere for 48 hours, then it is acidified with AcOH and evaporated in vacuum. After the usual work-up the residue, dissolved in AcOEt (25 ml), is added to a solution of fumaric acid (0.78 g) in MeOH (8 ml) at about 60° C., to give, after cooling, 3.2 g of 2-[2-aminopropyl)-thio]methyl-3-carboethoxy-5-carbomethoxy-4-(m-nitrophenyl)-6-methyl-1,4-dihydropyridine fumarate, m.p. 127°-130° C.

Using the above described procedure the following compounds are prepared:

2-[(2-amino-2-phenylethyl)thio]methyl-3-carboethoxy-5-carbomethoxy-4-(m-nitrophenyl)-6-methyl-1,4-dihydropyridine fumarate, m.p. 182°-184° C.;

2-[(2-aminopropyl)thio]methyl-3-carboethoxy-4-(m-nitrophenyl)-5-nitro-6-methyl-1,4-dihydropyridine fumarate, m.p. 148°-152° C.

EXAMPLE 34

A mixture of 2-[(2-aminoethyl)thio]methyl-3-carboethoxy-5-carbomethoxy-4-(m-nitrophenyl)-6-methyl-1,4-dihydropyridine (3.5 g), acetone (12 ml), AcOH (0.7 ml), sodium cyanoborohydride (0.6 g) and molecular sieves 4 A in EtOH (30 ml) is stirred under $N_2$ for 24 hours. After the usual work-up the residue is dissolved in AcOEt and saturated with gaseous HCl to precipitate 2.8 g of 2-[(2-N-isopropylaminoethyl)thio]methyl-3-carboethoxy-5-carbomethoxy-4-(m-nitrophenyl)-6-methyl-1,4-dihydropridine hydrochloride, m.p. 184°-186° C.

Using in the same procedure a salt (for example acetate or formate) of 2-[(5-amino-2-oxopentyl)thio]methyl and of 2-[(6-amino-2-oxohexyl)thio]methyl-3-carboethoxy-5-carbomethoxy-4-(m-nitrophenyl)-6-methyl-1,4-dihydropyridine, by intramolecular reductive amination, the following 3-carboethoxy-5-carbomethoxy-4-(m-nitrophenyl)-6-methyl-1,4-dihydropyridines are respectively obtained:

2-[(pyrrolidin-2-yl)methylthio]methyl, oil, NMR (CDCl$_3$); δ (TMS): 1.00–1.25 (3H, t); 1.50–2.00 (4H, m); 2.25 (3H, s); 2.40–3.00 (6H, m); 3.70 (3H, s); 3.80–4.10 (4H, m); 5.05 (1H, s); 7.20–8.10 (4H, m); 9.00–9.10 (1H, m);

2-[(piperidin-2-yl)methylthio]methyl, oil, NMR (CDCl$_3$); δ (TMS): 1.00–1.20 (3H, t); 1.50–2.20 (6H, m); 2.25 (3H, s); 2.50–3.10 (6H, m); 3.80–4.20 (7H, m); 5.10 (1H, s); 7.20–8.20 (5H, m).

EXAMPLE 35

A solution of 2-[(2-aminoethyl)thio]methyl-3,5-dicarboethoxy-4-(m-nitrophenyl)-6-methyl-1,4-dihydropyridine (1.35 g) and 2-hydroxy-3-methoxy-5-morpholinomethylbenzaldehyde (0.76 g) in EtOH (40 ml) is stirred at room temperature for 30 minutes to give the corresponding Schiff-base. Sodium borohydride (0.12 g) is then added and after 30 minutes the mixture is neutralized with AcOH to give, after the usual work-up, 1.7 g of 2-[2-[N-(2-hydroxy-3-methoxy-5-morpholinomethyl)benzylamino]ethylthio]methyl-3,5-dicarboethoxy-4-(m-nitrophenyl)-6-methyl-1,4-dihydropyridine, which yields, upon treatment with fumaric acid, the corresponding salt (m.p. 168°-170° C. $C_{34}H_{44}N_4SO_9.2.C_4H_4O_4.H_2O$).

EXAMPLE 36

According to the procedure described in the previous example the following compounds are prepared:

2-[2-[N-(2-hydroxy-5-methoxy-3-morpholinomethylbenzyl)-amino]ethylthio]methyl-3,5-dicarboethoxy-4-(m-nitrophenyl)-6-methyl-1,4-dihydropyridine difumarate hydrate, m.p. 102°-105° C.;

2-[2-[N-(4-hydroxy-3-methoxy-5-morpholinomethylbenzyl)-amino]ethylthio]methyl-3,5-dicarboethoxy-4-(m-nitrophenyl)-6-methyl-1,4-dihydropyridine difumarate hydrate, m.p. 175°-178° C.;

2-[4-(N-benzylamino)butyl]methyl-3,5-dicarboethoxy-4-(m-trifluoromethylphenyl)-6-methyl-1,4-dihydropyridine, 2-[2-(p-NO$_2$-benzylamino)ethylthio]methyl-3,5-dicarbomethoxy-4-(o-chlorophenyl)-6-methyl-1,4-dihydropyridine maleate.

EXAMPLE 37

A water solution of hydrazine (40%, 1.6 ml) is dropped at 7° C. in a solution of 2-[3-(N-phtalymido)-propylthio]methyl-3-carboethoxy-5-carbomethoxy-4-(m-nitrophenyl)-6-methyl-1,4-dihydropyridine (3.3 g) in EtOH (35 ml). After an hour, it is cooled to room temperature, the phthalhydrazide is filtered off and the eluate is evaporated to dryness, to give, after the usual work-up, 2.5 g of 2-[(3-aminopropyl)thio]methyl-3-carboethoxy-5-carbomethoxy-4-(m-nitrophenyl)-6-methyl-1,4-dihydropyridine. Using the salification procedure described in Example 23, 2.6 g of the corresponding fumarate is obtained, m.p. 142°-145° C.

According to the above described procedure, 2-[(4-aminobutyl)thio]methyl-3-carboethoxy-5-carbomethoxy-4-(m-nitrophenyl)-6-methyl-1,4-dihydropyridine fumarate, m.p. 109°-111° C., is obtained.

EXAMPLE 38

A solution of m-chloroperbenzoic acid (1.3 g, 1 equiv. mol.) in 1,2-dichloroethane (15 ml) is added at −10° C. to a solution of 2-[(2-aminoethyl)thio]methyl-3-carboethoxy-5-carbomethoxy-4-(m-nitrophenyl)-6-methyl-1,4-dihydrochloride hydrochloride (3.5 g) in 1,2-dichloroethane (30 ml).

After 30 minutes the solution is filtered, washed with sodium thiosulfate (5% water solution, 3×5 ml), sodium bicarbonate (saturated water solution 3×10 ml), water (3×10 ml), dried on Na$_2$SO$_4$ and evaporated in vacuum to give 3.2 g of 2-[(2-aminoethyl)sulfinyl]methyl-3-carboethoxy-5-carbomethoxy-4-(m-nitrophenyl)-6-methyl-1,4-dihydropyridine yielding, upon treatment with fumaric acid according to Example 23, the corresponding fumarate, m.p. 170°-172° C.

EXAMPLE 39

Using the procedure described in Example 38, the following compounds are prepared:

2-(methylsulfinyl)methyl-3,5-dicarboethoxy-4-(m-nitrophenyl)-6-methyl-1,4-dihydropyridine, m.p. 167°-169° C.;

2-(ethylsulfinyl)methyl-3,5-dicarboethoxy-4-(m-nitrophenyl)-6-methyl-1,4-dihydropyridine, m.p. 128°-130° C.;

2-[(2-aminoethyl)sulfinyl]methyl-3,5-dicarboethoxy-4-(m-nitrophenyl)-6-methyl-1,4-dihydropyridine, m.p. 140°-142° C.

EXAMPLE 40

A solution of m-chloroperbenzoic acid (3.76 g, 2 equiv. mol.) in MeOH (30 ml) is added at 10° C. to a solution of 2-[(2-aminoethyl)thio]methyl-3-carboethoxy-5-carbomethoxy-4-(m-nitrophenyl)-6-methyl-1,4-dihydropyridine fumarate (5 g) in MeOH (100 ml); the reaction mixture is then warmed to +15° C. and stirred for 30 minutes. The methanol is then evaporated under reduced pressure, the residue partitioned between dichloromethane (80 ml) and water (30 ml). The organic phase is washed with sodium thiosulfate (5% water solution, 2×10 ml), aqueous saturated NaHCO$_3$ solution (3×20 ml), water (3×20 ml), dried on Na$_2$SO$_4$ and evaporated to dryness to give 3.8 g of 2-[(2-aminoethyl)sulfonyl]methyl-3-carboethoxy-5-carbomethoxy-4-(m-nitrophenyl)-6-methyl-1,4-dihydropyridine which is salified with fumaric acid to give 4.3 g of the corresponding fumarate, m.p. 147°–149° C.

EXAMPLE 41

A solution of tert-butyl-4-chloroacetoacetate (7 g) in EtOH (20 ml) is added at 0° C. to a solution of the sodium salt of 2-(N-phtalimido)ethylmercaptane (7.5 g) in EtOH under N$_2$. After one hour the solution is neutralized with AcOH and evaporated to give, after the usual work-up, 9.3 g or ter-butyl 4-[2-(N-phtalimido)ethyl]thioacetoacetate, m.p. 4°–77° C.

A solution of this compound (8.8 g), m-nitrobenzaldehyde (3.7 g), AcOH (0.6 ml) and piperidine (0.2 ml) in benzene (90 ml) is heated to reflux for 4 hours in a Dean-Stark apparatus to give, after the usual work-up, 11.2 g of tert-butyl 2-(m-nitrophenylmethylen)-4-[2-(N-phtalimidoethyl)thioacetoacetate as an oil.

A solution of this compound (10 g) and methyl 3-aminocrotonate (2.4 g) in EtOH (150 ml) is heated to reflux temperature for two hours then acidified (pH ≃ 1) with aqueous concentrated HCl (0.5 ml) cooled to room temperature and stirred for one hour before evaporation to dryness. The residue, after the usual work-up, yields 7 g of 2-[2-(N-phtalimido)ethylthio-methyl-3-carbotertbutoxy-5-carbomethoxy-4-m-nitrophenyl)-6-methyl-1,4-dihydropyridine, m.p. 65°–70° C.

0.2 g are dissolved at 0° C. in dichloromethane (4 ml) and trifluoroacetic acid (4 ml). After six hours the mixture is evaporated to dryness to give, after the usual work-up, 0.08 g of the corresponding 3-carboxy acid derivative.

EXAMPLE 42

A solution of 2-(2-aminoethylthio)methyl-3,5-dicarboethoxy-4-(m-nitrophenyl)-6-methyl-1,4-dihydropyridine (4.35 g) and acetic anhydride (10 ml) in pyridine (25 ml) is stirred at room temperature for two hours, then it is poured in iced water (250 ml) and extracted with AcOEt (3×30 ml).

The organic phase is washed with H$_2$SO$_4$ (2N, 2×10 ml), water (4×25 ml), dried on Na$_2$SO$_4$ and evaporated in vacuum. The residue is crystallized from Et$_O$ $_{to\ give}$ 4.6 g of 2-[(2-N-acetylaminoethyl)thio]methyl-3,5-dicarboethoxy-4-(m-nitrophenyl)-6-methyl-1,4-dihydropyridine, m.p. 68°–71° C.

Using the same procedure, 2-[(2-acetoxyethyl)-thio]-methyl-3,5-dicarboethoxy-4-(m-nitrophenyl)-6-methyl-1,4-dihydropyridine (m.p. 84°–86° C.) is obtained starting from the corresponding 2-[(2-hydroxyethyl)thio]-methyl-dihydropyridine.

EXAMPLE 43

S-(N-Tertbutoxycarbonyl)prolinol (4.0 g) is transformed by reaction with tosylchloride (4.5 g) in pyridine (20 ml), into S-(N-tert-butoxycarbonyl)prolinol-tosylate (6 g). A solution of this compound (6 g) in EtOH (60 ml) is reacted with potassium thioacetate (6 g) at the reflux temperature for 40 minutes to give, after the usual work-up, 3.2 g of S-2-acetylthiomethyl-1-tert-butoxycarbonyl-pyrrolidine.

A solution of this compound (3.2 g) is stirred at 0° C., under nitrogen, in EtOH (30 ml) and sodium hydroxide (1N, 14 ml); after 20 minutes a solution of 4-R,S-2-chloromethyl-3-carboethoxy-5-carbomethoxy-4-(m-nitrophenyl)-6-methyl-1,4-dihydropyridine (4.5 g) in EtOH/DME (1/1, 40 ml) is added dropwise. After one hour the mixture is neutralised with AcOH and evaporated to dryness to give, after the usual work-up and column-chromatography purification (SiO$_2$, 250 g, eluent: hexane/AcOEt 75/25) 4.3 g of 2'-(S)-4(R,S)-2-[(1'-tert-butoxycarbonylpyrrolidin-2'-yl)methylthio]methyl-3-carboethoxy-5-carboethoxy-5-carbomethoxy-4-(m-nitrophenyl)-6-methyl-1,4-dihydropyridine (oil).

NMR (CDCl$_3$); δ (TMS): 1.10–1.70 (12H, m); 1.70–2.10 (4H, m); 2.30 (3H, s); 3.20–4.30 (12H, m); 5.10 (1H, s); 7.10–8.20 (5H, m).

The tert-butoxycarbonyl protective group is removed by treatment of a solution of the compound (3.6 g) in 1,2-dichloroethane (20 ml) with trifluoroacetic acid (20 ml) at 0° C. for two hours. The reaction mixture is evaporated in vacuum to dryness, the residue is dissolved in water (50 ml), and washed with Et$_2$O (3×20 ml). The aqueous phase is made basic with NaHCO$_3$ and extracted with Et$_2$O (3×60 ml). The organic layer is dried on Na$_2$SO$_4$ and evaporated to dryness to give 2.75 g of 2'(S)-4-(R,S)-2-[(pyrrolidin-2'-yl)methylthio]methyl-3-carboethoxy-5-carbomethoxy-4-(m-nitrophenyl)-6-methyl-1,4-dihydropyridine as an oil.

The fractional crystallization from AcOEt of the diastereoisomeric mixture gives one diastereoisomer, m.p. 154°–155° C., [α]$_D$ = −88° C. (C=1%, CHCl$_3$). Further recrystallizations of the motor liquors from AcOEt/Et$_2$O (1/1) yields the other diastereoisomer, m.p. 114°–116° C., [α]$_D$ = −14° C. (C=1%, CHCl$_3$).

Using in the procedure described above (R)-(N-tert-butoxycarbonyl)prolinol the following 3-carboethoxy-5-carbomethoxy-4-(m-nitrophenyl)-6-methyl-1,4-dihydropyridine derivatives are obtained:
2'(R)-4(R)-2-(pyrrolidin-2'-yl)methylthio-methyl;
2'(R)-4(S)-2-(pyrrolidin-2'-yl)methylthio-methyl.

EXAMPLE 44

A solution of methyl acetoacetate (7 g), 2-(N-benzyl-N-methylamino)ethanol (3 g) and 4-N,N-dimethylaminopyridine (2 g) in toluene is heated to reflux for 16 hours to give, after the usual work-up and purification on column chromatography (SiO$_2$, 2.0 g; eluent: methylene chloride), 3 g of 2-(N-benzyl-N-methylamino)ethyl acetoacetate, m.p. 45°–47° C.

A solution of this compound (3 g) and ammonium acetate (2 g) in EtOH (30 ml) is heated to the reflux temperature for one hour, then ethyl 2-(m-nitrophenyl-methylen)-4-chloro-3-oxo-butanoate (3.4 g) is added thereto. After 30 minutes, the reaction mixture is cooled to room temperature, acidified (pH ≃ 1) with aqueous concentrated HCl (0.2 ml), stirred for one hour, neutralized with NaHCO$_3$ and evaporated under reduced pressure, to give, after the usual work-up, 2.5 g of 2-chloromethyl-3-carboethoxy-5-[2-(N-benzyl-N-methylamino)ethoxy]carbonyl-4-(m-nitrophenyl)-6-methyl-1,4-dihydropyridine, oil.

NMR (CDCl$_3$); δ (TMS): 1.00–1.25 (3H, t); 2.10–2.20 (6H, m); 2.50–2.80 (4H, m); 3.30–3.50 (2H, s); 3.80–4.40 (2H, q); 4.60–5.10 (2H, dd); 5.20 (1H, s); 6.80–8.20 (10H, m).

An ethanol solution (10 ml) of this compound (1.9 g) is added to a solution of cysteamine hydrochloride (0.43 g) and sodium hydroxide (20% water solution, 0.6 ml) in ethanol (20 ml) according to the procedure of Example 23 to give after the usual work-up, 1.5 g of 2-[(2-aminoethyl)thio]methyl-3-carboethoxy-5-[2-(N-benzyl-N-methylamino)ethoxy]carbonyl-4-(m-nitrophenyl)-6-methyl-1,4-dihydropyridine, oil.

NMR (CDCl$_3$); δ (TMS): 1.10–1.25 (3H, t); 2.10–2.20 (6H, m); 2.30–3.20 (10H, m); 3.30–3.50 (2H, s); 3.80–4.40 (4H, m); 5.10 (1H, s); 6.80–8.20 (10H, m).

EXAMPLE 45

A solution of 2-[(2-aminoethyl)thio]methyl-3,5-dicarboethoxy-4-(m-nitrophenyl)-6-methyl-1,4-dihydropyridine (4.3 g) and acrylonitrile (0.8 g) in EtOH (60 ml) is heated to reflux for two hours, then it is cooled to room temperature and evaporated to dryness, to give, after the usual work-up, 4.2 g of 2-[2-N-(2-cyanoethyl)aminoethylthio]methyl-3,5-dicarboethoxy-4-(m-nitrophenyl)-6-methyl-1,4-dihydropyridine, which upon treatment with fumaric acid according to the salification procedure described in Example 23, gives 4 g of the corresponding fumarate, m.p. 105°–107° C.

Using in the above described procedure ethyl acrylate and acrylamide, the following 3,5-dicarboethoxy-6-methyl-1,4-dihydropyridine are obtained:
2-[2-N-(2-carboethoxyethyl)aminoethylthio]-4-(o-chlorophenyl);
2-[2-N-(2-carbamoylethyl)aminoethylthio]-4-(β-pyridyl).

EXAMPLE 46

A solution of 2-[2-aminoethylthio]methyl-3,5-dicarboethoxy-4-(m-nitrophenyl)-6-methyl-1,4-dihydropyridine 1 g), 2-chloroacetamide (0.26 g) and triethylamine (0.28 g) is refluxed for 24 hours, cooled at room temperature, evaporated to dryness, to give, after the usual work-up, and purification by column-chromatography (SiO$_2$, 30 g; eluent: CHCl$_3$/MeOH 95/5), 0.5 g of 2-[2-N-(carbamoylmethyl)-aminoethylthio]methyl-3,5-dicarboethoxy-4-(m-nitrophenyl)-6-methyl-1,4-dihydropyridine as an amorphous solid.

NMR (CDCl$_3$): δ 1.0–1.30 (6H, t); 2.30 (3H, s); 2.50–2.85 (5H, m); 3.20 (2H, s); 3.85–4.25 (6H, m); 5.10 (1H, s); 6.30 (1H, m); 7.00–8.2 (6H, m).

EXAMPLE 47

A solution of 2-mercaptomethyl-3-carboethoxy-5-cyano-4-(m-nitrophenyl)-6-methyl-1,4-dihydropyridine (3 g), 2-chloroacetonitrile (1 g) and 1,4-diazabicyclo-2,2,2-octane (0.8 g) in EtOH (30 ml) is heated at reflux temperature for six hours. Then the reaction is cooled to room temperature and after usual work-up and purification by columnchromatography (SiO$_2$ 90 g; eluent Et$_2$O/AcOEt 90/10) gives 1.8 g of 2-(cyanomethylthio)-methyl-3-carboethoxy-5-cyano-4-(m-nitrophenyl)-6-methyl-1,4-dihydropyridine.

EXAMPLE 48

Using in the procedure of Example 47 a suitable 2-mercaptomethyl-1,4-dihydropyridine and an activated chlorocompound the following compounds are obtained:
2-(2-cyanomethyl)-3-carboethoxy-5-nitro-4-(m-nitrophenyl)-6-methyl-1,4-dihydropyridine;
2-(2-ethoxycarbonylmethylthio)methyl-3-carboethoxy-5-cyano-4-(m-chlorophenyl)-6-methyl-1,4-dihydropyridine.

We claim:

1. A compound of formula I

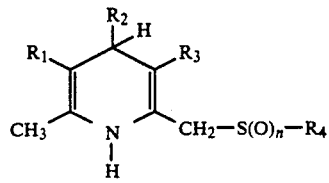

wherein:
R$_1$ is a group of formula CO$_2$R$_5$:
R$_2$ is a phenyl ring unsubstituted or substituted with a member selected from the group consisting of C$_1$–C$_6$ alkyl, C$_1$–C$_6$ alkoxy, halo-C$_1$–C$_4$ alkoxy, halo-C$_1$–C$_6$ alkyl, halogen, nitro, cyano, C$_1$–C$_6$ alkoxycarbonyl, C$_1$–C$_6$ alkylthio, C$_1$–C$_6$ alkylsulphinyl; or R$_2$ is pentafluorophenyl;
R$_3$ is a group of formula CO$_2$R$_5$;
R$_4$ is
a C$_2$–C$_{12}$ alkyl group unsubstituted of substituted by two dissimilar substituents selected from the group consisting of:
hydroxy;
thio;
cyano;
halogen;
amino;
monobenzylamino;
benzyl(C$_1$–C$_2$)alkylamino;
C$_1$–C$_4$ alkoxy;
C$_1$–C$_4$ alkylthio;
C$_1$–C$_4$ acyloxy;
C$_1$–C$_4$ acylthio;
CO$_2$H;
C$_1$–C$_4$ alkoxycarbonyl;
CONR$_6$R$_7$;
a C$_3$–C$_7$ cycloalkyl;
n is 0, 1 or 2;
R$_5$ is hydrogen, a cation of ammonium or of an alkaline metal; a C$_1$–C$_6$ alkyl chain unsubstituted or substituted by hydroxy, amino, mono(C$_1$–C$_3$)alkylamino, benzylamino, di(C$_1$–C$_2$)alkylamino, benzyl(C$_1$–C$_2$)alkylamino, C$_1$–C$_6$ alkoxy; or C$_3$–C$_6$ alkenyl;
each of R$_6$ and R$_7$, which are the same or different, may be hydrogen, C$_1$–C$_6$ alkyl, benzyl or phenyl;
or a pharmaceutically acceptable salt thereof.

2. A compound according to claim 1, wherein n is zero.

3. A compound according to claim 2, wherein R$_1$ and R$_3$ are (loweralkoxy) carbonyl groups.

4. A compound selected from the group consisting of
2-[2-oxopentyl)thio]methyl-3-carboethoxy-5-carbomethoxy-4-(m-nitrophenyl)-6-methyl-1,4-dihydropyridine,
2-[2-oxopropyl)thio]methyl-3-carboethoxy-5-carbomethoxy-4-(m-nitrophenyl)-6-methyl-1,4-dihydropyridine,
2-[(3-carboethoxy-2-oxopropyl)thio]methyl-3-carboethoxy-5-carbomethoxy-4-(m-nitrophenyl)-6-methyl-1,4-dihydropyridine, 2-[(2-phenyl-2-oxoethyl)thio]methyl-3-carboethoxy-5-carbomethoxy-4-(m-nitrophenyl)-6-methyl-1,4-dihydropyridine, 2-[(3-phenyl-2-oxopropyl)thio]methyl-3-carboethoxy-5-carbomethoxy-4-(m-trifluoromethylphenyl)-6-methyl-1,4-dihydropyridine, 2-[(5-acetylamino-2-oxopentyl)thio]methyl-3-carboethoxy-5-carbomethoxy-4-(m-nitrophenyl)-6-methyl-1,4-dihydropyridine, 2-[(6-acetylamino-2-oxohexyl)thio]methyl-3-carboethoxy-5-carbomethoxy-4-(m-nitrophenyl)-6-methyl-1,4-dihydropyridine, 2-[(2,2-diethoxyethyl)thio]methyl-3-carboethoxy-5-carbomethoxy-4-(m-nitrophenyl)-6-methyl-1,4-dihydropyridine, 2-[(2,2-dimethoxyethyl)thio]methyl-3-carboethoxy-5-carbomethoxy-4-(m-trifluoromethylphenyl)-6-methyl-1,4-dihydropyridine, 2-[(formylmethyl)thio]methyl-3-carboethoxy-5-carbomethoxy-4-(m-nitrophenyl)-6-methyl-1,4-dihydropyridine, 2-[(glutathione-S-yl)thio]methyl-3,5-dicarboethoxy-4-(m-nitrophenyl)-6-methyl-1,4-dihydropyridine, 2-[(glutathione-S-yl-diethylester)thio]methyl-3,5-dicarboethoxy-4-(m-nitrophenyl)-6-methyl-1,4-dihydropyridine, 2-[(2-carbomethoxy-2-aminoethyl)thio]methyl-3,5-dicarboethoxy-4-(m-trifluoromethylphenyl)-6-methyl-1,4-dihydropyridine, 2-[(3-amino-2-hydroxypropyl)thio]methyl-3-carboethoxy-5-carbomethoxy-4-(m-nitrophenyl)-6-methyl-1,4-dihydropyridine, 2[(3-hydroxy-2-amino-propyl)thio]methyl-3-carboethoxy-5-carbomethoxy-4-(m-nitrophenyl)-6-methyl-1,4-dihydropyridine, 2-[(3-oxo-1-phenylpropyl)thio]methyl-3,5-dicarboethoxy-4-(m-nitrophenyl)-6-methyl-1,4-dihydropyridine, 2-[(3-oxo-cyclohexane-1-yl)thio]methyl-3,5-carboethoxy-4-(m-nitrophenyl)-6-methyl-1,4-dihydropyridine, or a pharmaceutically acceptable salt thereof.

5. A pharmaceutical composition for treating hypertensive conditions or for inducing an antithrombotic, cytoprotective or antiulcer condition, said composition comprising an effective amount of a compound of claim 1 and a pharmaceutically acceptable carrier.

6. A method of producing an antihypertensive condition in a patient in need of such condition, said method comprising administering to said patient an antihypertensive effective amount of a compound of claim 1.

7. A compound according to claim 1, wherein said compound is selected from the group consisting of:

2-[(formylmethyl)thio]methyl-3-carboethoxy-5-carbomethoxy-4-(m-nitrophenyl)-6-methyl-1,4-dihydropyridine, 2-[(2-carbomethoxy-2-aminoethyl)thio]methyl-3,5-dicarboethoxy-4-(m-trifluoromethylphenyl)-6-methyl-1,4-dihydropyridine, 2-[(3-amino-2-hydroxpropyl)thio]methyl-3-carboethoxy-5-carbomethoxy-4-(m-nitrophenyl)-6-methyl-1,4-dihydropyridine, 2-[(3-hydroxy-2-amino-propyl)thio]methyl-3-carboethoxy-5-carbomethoxy-4-(m-nitrophenyl)-6-methyl-1,4-dihydropyridine, 2-[(2-amino-2-phenylethyl)thio]methyl-3-carboethoxy-5-carbomethoxy-4-(m-nitrophenyl)-6-methyl-1,4-dihydropyridine fumarate, and a pharmaceutically acceptable salt thereof.

8. A compound selected from the group consisting of:

2-[2-oxopentyl)thio]methyl-3-carboethoxy-5-carbomethoxy-4-(m-nitrophenyl)-6-methyl-1,4-dihydropyridine, 2-[2-oxopropyl)thio]methyl-3-carboethoxy-5-carbomethoxy-4-(m-nitrophenyl)-6-methyl-1,4-dihydropyridine, 2-[(3-carboethoxy-2-oxopropyl)thio]methyl-3-carboethoxy-5-carbomethoxy-4-(m-nitrophenyl)-6-methyl-1,4-dihydropyridine, 2-[(2-phenyl-2-oxoethyl)thio]methyl-3-carboethoxy-5-carbomethoxy-4-(m-nitrophenyl)-6-methyl-1,4-dihydropyridine, 2-[(3-phenyl-2-oxopropyl)thio]methyl-3-carboethoxy-5-carbomethoxy-4-(m-trifluoromethylphenyl)-6-methyl-1,4-dihydropyridine, 2-[(5-acetylamino-2-oxopentyl)thio]methyl-3-carboethoxy-5-carbomethoxy-4-(m-nitrophenyl)-6-methyl-1,4-dihydropyridine, and 2-[(6-acetylamino-2-oxohexyl)thio]methyl-3-carboethoxy-5-carbomethoxy-4-(m-nitrophenyl)-6-methyl-1,4-dihydropyridine.

* * * * *

UNITED STATES PATENT AND TRADEMARK OFFICE
CERTIFICATE OF CORRECTION

PATENT NO. : 5,021,436
DATED : June 4, 1991
INVENTOR(S) : GANDOLFI et al

It is certified that error appears in the above-identified patent and that said Letters Patent is hereby corrected as shown below:

On the cover page, Item [75], "Sengio" should read -- Sergio--.

Signed and Sealed this

Thirteenth Day of October, 1992

Attest:

DOUGLAS B. COMER

*Attesting Officer*      Acting Commissioner of Patents and Trademarks